US012159707B2

(12) United States Patent
Lewis

(10) Patent No.: US 12,159,707 B2
(45) Date of Patent: Dec. 3, 2024

(54) HOME HEALTH MONITORING OF PATIENTS VIA EXTENSION OF HEALTHCARE SYSTEM NETWORK INTO CUSTOMER PREMISES

(71) Applicant: CenturyLink Intellectual Property LLC, Broomfield, CO (US)

(72) Inventor: Ronald A. Lewis, Montgomery, AL (US)

(73) Assignee: CenturyLink Intellectual Property LLC, Denver, CO (US)

( * ) Notice: Subject to any disclaimer, the term of this patent is extended or adjusted under 35 U.S.C. 154(b) by 518 days.

(21) Appl. No.: 17/037,280

(22) Filed: Sep. 29, 2020

(65) Prior Publication Data

US 2022/0059216 A1    Feb. 24, 2022

Related U.S. Application Data

(60) Provisional application No. 63/068,072, filed on Aug. 20, 2020.

(51) Int. Cl.
*G16H 40/20* (2018.01)
*G06F 21/60* (2013.01)
(Continued)

(52) U.S. Cl.
CPC .......... *G16H 40/20* (2018.01); *G06F 21/602* (2013.01); *G06F 21/6245* (2013.01);
(Continued)

(58) Field of Classification Search
CPC ........ G16H 10/60; G16H 20/17; G16H 20/30; G16H 40/20; G16H 80/00
(Continued)

(56) References Cited

U.S. PATENT DOCUMENTS

2008/0155094 A1* 6/2008 Roese ................. G01S 5/02
  709/224
2009/0019552 A1* 1/2009 McLaughlin .......... G16H 10/65
  705/3
(Continued)

FOREIGN PATENT DOCUMENTS

KR      20120017079 A  *  2/2012

OTHER PUBLICATIONS

Salih, Raed M; Using Agent-Based Implementation of Active Data Bundles for Protecting Privacy in Healthcare Information Systems;: Western Michigan University. ProQuest Dissertations Publishing, 2018. 10904609. (Year: 2018).*
(Continued)

*Primary Examiner* — Hiep V Nguyen

(57) ABSTRACT

Novel tools and techniques are provided for implementing home health monitoring of patients via extension of healthcare system network into customer premises. In various embodiments, a computing system might receive, wirelessly from a data collector assigned to a patient, collected patient data obtained by a patient device(s) associated with the patient. The computing system and/or a management console might establish a network transport link between the computing system and a healthcare data system that is accessible by a healthcare provider(s), and might send the patient data over the network transport link to the healthcare data system. The management console might store the patient data in a portion of the healthcare data system that is allocated to information regarding the patient, wherein the network transport link is configured as a one-way link that prevents access to any data stored in the healthcare data system via the one-way link.

19 Claims, 7 Drawing Sheets

(51) Int. Cl.
  *G06F 21/62* (2013.01)
  *G06Q 30/018* (2023.01)
  *G06Q 50/26* (2024.01)
  *G16H 10/60* (2018.01)
  *G16H 20/13* (2018.01)
  *G16H 20/17* (2018.01)
  *G16H 20/30* (2018.01)
  *G16H 20/60* (2018.01)
  *G16H 40/67* (2018.01)
  *H04L 9/40* (2022.01)
  *H04W 4/80* (2018.01)
  *H04W 76/10* (2018.01)

(52) U.S. Cl.
  CPC ....... *G06Q 30/0185* (2013.01); *G06Q 50/265* (2013.01); *G16H 10/60* (2018.01); *G16H 20/13* (2018.01); *G16H 20/17* (2018.01); *G16H 20/30* (2018.01); *G16H 20/60* (2018.01); *G16H 40/67* (2018.01); *H04W 4/80* (2018.02); *H04W 76/10* (2018.02); *H04L 63/0272* (2013.01)

(58) Field of Classification Search
  USPC .............................................. 705/2
  See application file for complete search history.

(56) References Cited

U.S. PATENT DOCUMENTS

2012/0017079 A1* 1/2012 Mraz .................... H04L 9/3236
  713/153
2012/0242501 A1* 9/2012 Tran .................... A61B 5/4875
  340/870.02

OTHER PUBLICATIONS

Ozano, Kimberley; Mind the Gap! An Investigation into the Optimisation of Public Health Skills, Knowledge and Practices of Health Workers in Cambodia; Liverpool John Moores University (United Kingdom). ProQuest Dissertations & Theses, 2017. 10755511. (Year: 2017).*

* cited by examiner

HOME HEALTH MONITORING OF PATIENTS VIA EXTENSION OF HEALTHCARE SYSTEM NETWORK INTO CUSTOMER PREMISES

CROSS-REFERENCES TO RELATED APPLICATIONS

This application claims priority to U.S. Patent Application Ser. No. 63/068,072 (the "'072 Application"), filed Aug. 20, 2020 by Ronald A. Lewis, entitled, "Home Health Monitoring of Patients via Extension of Healthcare System Network into Customer Premises," the disclosure of which is incorporated herein by reference in its entirety for all purposes.

This application may be related to U.S. patent application Ser. No. 17/037,258, by Ronald A. Lewis, filed on Sep. 29, 2020, now issued as U.S. Pat. No. 11,178,043, entitled, "Prioritized Data Routing Over Message Brokering System Network for Connected Devices," which claims priority to U.S. Patent Application Ser. No. 63/068,066 (the "'066 application"), filed Aug. 20, 2020 by Ronald A. Lewis and titled, "Prioritized Data Routing over Message Brokering System Network for Connected Devices", the disclosure of which is incorporated herein by reference in its entirety for all purposes.

This application may also be related to U.S. patent application Ser. No. 15/370,764 (the "'764 application"), filed Dec. 6, 2016 by Thomas C. Barnett, Jr. and titled, "Internet of Things (IoT) Human Interface Apparatus, System, and Method", which claims priority to U.S. Patent Application Ser. No. 62/342,710 (the "'710 application"), filed May 27, 2016 by Thomas C. Barnett, Jr. and titled, "Internet of Things (IoT) Human Interface Apparatus, System, and Method", the disclosure of each of which is incorporated herein by reference in its entirety for all purposes.

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing health monitoring of patients, and, more particularly, to methods, systems, and apparatuses for implementing home health monitoring of patients via extension of healthcare system network into customer premises.

BACKGROUND

Doctors need to be able to remotely monitor patient health conditions (e.g., home health), but there is a shortage of skilled home health workers to collect key health data. Although conventional devices exist that collect data automatically, these conventional devices still require home health works to act as "data brokers" to retrieve the collected data and enter the information onto forms and to manually hand or to transmit the data or forms to the doctor or some other healthcare provider, who would then enter the data and interpretations of the data into an electronic medical record ("EMR") or an electronic health record ("EHR") associated with the patient.

Hence, there is a need for more robust and scalable solutions for implementing health monitoring of patients, and, more particularly, to methods, systems, and apparatuses for implementing home health monitoring of patients via extension of healthcare system network into customer premises.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Overview

Figure 1:
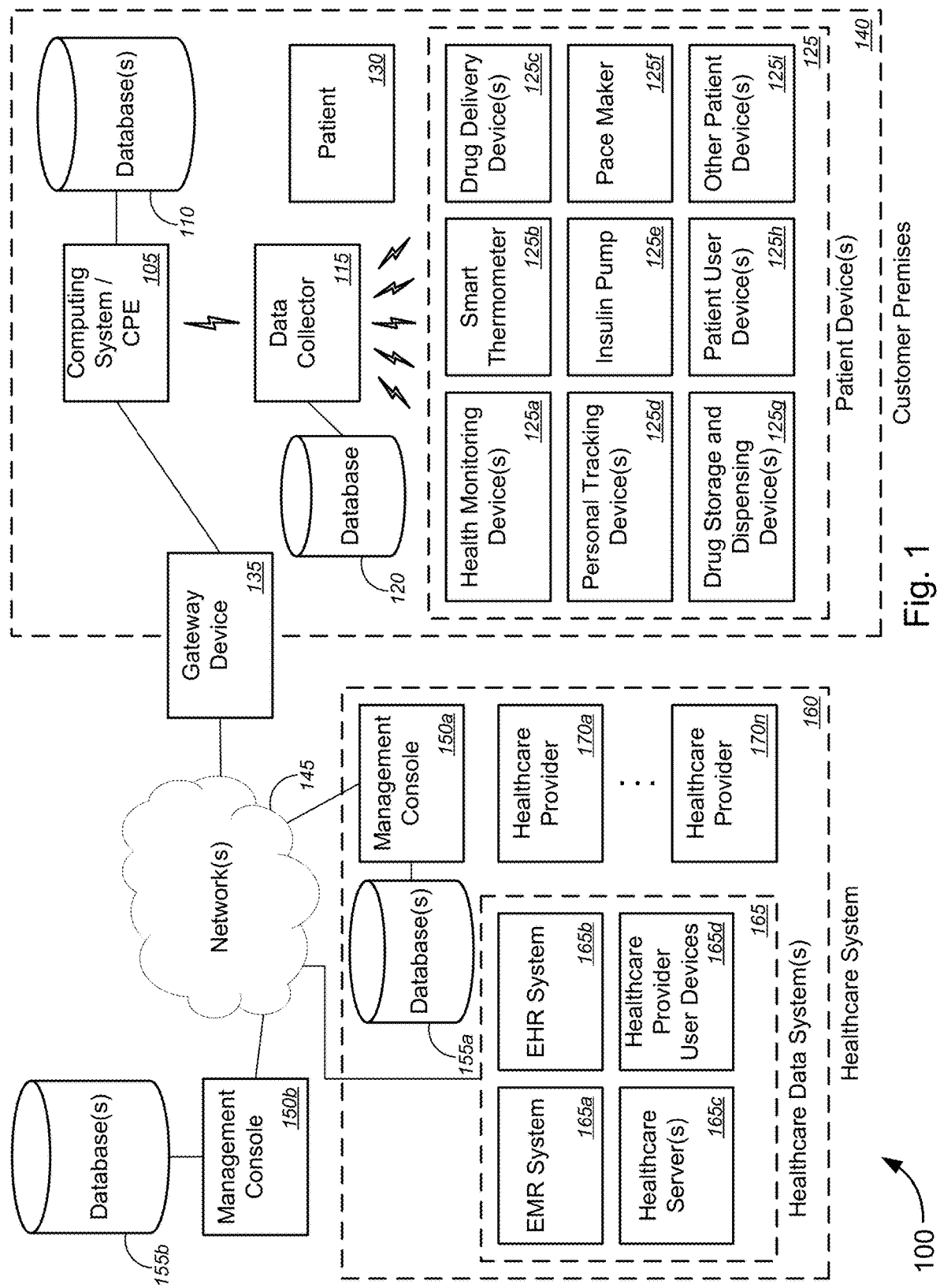
FIG. 1 is a schematic diagram illustrating a system for implementing home health monitoring of patients via extension of healthcare system network into customer premises, in accordance with various embodiments.

Various embodiments provide tools and techniques for implementing health monitoring of patients, and, more particularly, to methods, systems, and apparatuses for implementing home health monitoring of patients via extension of healthcare system network into customer premises.

In various embodiments, to properly assess the health of a patient, a healthcare provider (e.g., a doctor, or the like) might hand out, assign, or prescribe one or more first patient devices (and perhaps a data collector as well) to the patient.

The patient would be asked to wear or attach the one or more first patient devices on the patient's body or clothing (or to implant the one or more first patient devices in the patient's body), the one or more first patient devices being registered on a healthcare data system(s) and/or the management console as being associated with the patient. The management console or the system might then extend the healthcare system network to each customer local area network in a customer premises of the patient among a plurality of customer local area networks in corresponding customer premises associated with a corresponding plurality of patients, in the manner described below. In this way, patient privacy and security, as well as compliance with standards such as the standards set out in the health insurance portability and accountability act ("HIPAA") may be achieved.

That is, in operation, when the patient returns to the patient's customer premises with the assigned one or more first patient devices (and, in some cases, the assigned data collector as well), where the one or more first patient devices are assigned to the patient concurrent with the data collector being assigned to the patient, the one or more first patient devices may be pre-paired with the data collector, enabling the one or more first patient devices to automatically wirelessly communicate with the data collector when both are (simultaneously or concurrently) activated at the customer premises. Alternatively, where the one or more first patient devices are assigned to the patient after the data collector has been assigned to the patient and has been collecting data from other patient devices among the one or more patient devices, the one or more first patient devices may each be added and registered as a new device that is associated with at least one of the patient or the data collector, enabling the one or more first patient devices to automatically synchronize, and wirelessly communicate, with the data collector when both are (simultaneously or concurrently) activated at the customer premises.

Once paired, the data collector might establish a paired wireless link between the data collector and each of at least one patient device among one or more patient devices assigned to the patient. In some instances, the at least one data collector might include, but is not limited to, a unique authentication token that is hard-coded in the at least one data collector. The data collector might receive and collect first patient data from each of at least one patient device among the one or more patient devices over the corresponding paired wireless link. In some instances, the first patient data might include, but is not limited to, at least one of data regarding physiology of the patient, health tracking data of the patient, or data regarding a health alert associated with the patient, and/or the like. In some cases, the first patient data might be encrypted at each of the at least one patient device prior to sending to the data collector. Computing system might establish a wireless link between the computing system and the data collector, which might relay the collected first patient data to the computing system via the established wireless link. In some embodiments, the paired wireless link (between the data collector and each of at least one patient device) and/or the wireless link (between the computing system and the data collector) might each include, without limitation, at least one of a Bluetooth wireless link, a WiFi wireless link, a ZigBee wireless link, or Z-wave wireless link, and/or the like. The computing system might receive, from the data collector, the first patient data obtained by at least one patient device that is associated with and assigned to the patient.

At least one of the computing system or the management console might establish a first network transport link between the computing system and at least one healthcare data system that is accessible by or associated with one or more healthcare providers. According to some embodiments, the first network transport link might include, without limitation, at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system is disposed, and/or the like. At least one of the computing system or the management console might send the first patient data over the first network transport link to the at least one healthcare data system. The management console might store the first patient data in the at least one healthcare data system, the first patient data being secured within a portion of the at least one healthcare data system that is allocated to information regarding the patient. In some embodiments, the first network transport link might be configured as a one-way network transport link that enables storage of the first patient data from the data collector to the at least one healthcare data system while preventing access to any data stored in the at least one healthcare data system via the first network transport link.

In some embodiments, the management console might establish a second network transport link between the management console and at least one of the computing system or the first data collector. In some cases, the second network transport link, like the first network transport link, might include, without limitation, at least one of a VPN, a SD-LAN, a SD-WAN, or a virtual extension of the healthcare provider network in which the at least one healthcare data system is disposed, and/or the like. In some instances, the management console might provide patient device data to the at least one of the computing system or the data collector over the second network transport link, the patient device data comprising a list of authorized patient devices among the one or more patient devices that are associated with and assigned to the patient. In some cases, providing the patient device data might comprise at least one of sending the patient device data to the computing system or providing the computing system with access over the second network transport link to a database containing the list of authorized patient devices associated with and assigned to the patient. In some instances, the at least one of the computing system or the data collector might prevent collection of data, or prevent communication of data (to the computing system and/or to the data collector), from devices that are not listed in the patient device data as being authorized. In some embodiments, the second network transport link and the first network transport link might be the same network transport link, while, in alternative embodiments, the second network transport link might be different or separate from the first network transport link. According to some embodiments, the management console might send communications data to at least one patient device among the one or more patient devices via the computing system over the second network transport link. In some instances, the communications data might include, without limitation, at least one of data regarding drug prescriptions for the patient, data regarding fitness regime, or data regarding diet, and/or the like.

Importantly, the various embodiments utilize automation to eliminate the need for manual data collection using home health, as well as leveraging data protection and data replication across a home network pipe that make full use of the features of virtual private network ("VPN") and/or software defined wide area network ("SD-WAN") technologies, or the like.

These and other aspects of the home health monitoring of patients via extension of healthcare system network into customer premises are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, home health technology, patient health monitoring technology, secure network extension technology, data segregation technology, and/or the like. In other aspects, certain embodiments, can improve the functioning of user equipment or systems themselves (e.g., home health system, patient health monitoring system, secure network extension system, data segregation system, etc.), for example, by receiving, with a computing system and from a first data collector, first patient data obtained by one or more patient devices that are associated with and assigned to a first patient, the first patient data being wirelessly collected from the one or more patient devices by the first data collector, the first data collector being assigned to the first patient, wherein the computing system and the first data collector are both located at a first customer premises associated with the first patient; establishing, with at least one of the computing system or a management console, a first network transport link between the computing system and at least one healthcare data system that is accessible by or associated with one or more healthcare providers; sending, with at least one of the computing system or the management console, the first patient data over the first network transport link to the at least one healthcare data system; and storing, with the management console, the first patient data in the at least one healthcare data system, the first patient data being secured within a portion of the at least one healthcare data system that is allocated to information regarding the first patient, wherein the first network transport link is configured as a one-way network transport link that enables storage of the first patient data from the first data collector to the at least one healthcare data system while preventing access to any data stored in the at least one healthcare data system via the first network transport link; and/or the like.

In particular, to the extent any abstract concepts are present in the various embodiments, those concepts can be implemented as described herein by devices, software, systems, and methods that involve specific novel functionality (e.g., steps or operations), such as, establishing secure network transport links (e.g., virtual private networks ("VPNs") and/or Internet Protocol security ("IPsec") tunnels, etc.) in a software defined wide area network ("SD-WAN") that is configured to by the management console to extend from a healthcare provider system to a data collector at a customer premises, collecting patient data autonomously from patient devices that monitor the patient's health condition, autonomously transferring or mirroring the patient data that is stored the data collector in an electronic medical record ("EMR") or an electronic health record ("EHR") associated with the patient that are part of a healthcare data system that aggregates patient data for each patient among a plurality of patients, and preventing access of the data via the network transport links and via other portions of the healthcare data system, and/or the like, to name a few examples, that extend beyond mere conventional computer processing operations. These functionalities can produce tangible results outside of the implementing computer system, including, merely by way of example, optimized and automated collection of patient data in a home health implementation (i.e., by extending the healthcare system network to the patient's customer premises local area network) that allows for efficient and secure transfer of sensitive patient data while eliminating the need for manual data collection, and/or the like, at least some of which may be observed or measured by patients, healthcare providers, and/or service providers.

In an aspect, a method might comprise receiving, with a computing system and from a first data collector, first patient data obtained by one or more patient devices that are associated with and assigned to a first patient, the first patient data being wirelessly collected from the one or more patient devices by the first data collector, the first data collector being assigned to the first patient, wherein the computing system and the first data collector are both located at a first customer premises associated with the first patient; establishing, with at least one of the computing system or a management console, a first network transport link between the computing system and at least one healthcare data system that is accessible by or associated with one or more healthcare providers; sending, with at least one of the computing system or the management console, the first patient data over the first network transport link to the at least one healthcare data system; and storing, with the management console, the first patient data in the at least one healthcare data system, the first patient data being secured within a portion of the at least one healthcare data system that is allocated to information regarding the first patient, wherein the first network transport link is configured as a one-way network transport link that enables storage of the first patient data from the first data collector to the at least one healthcare data system while preventing access to any data stored in the at least one healthcare data system via the first network transport link.

In some embodiments, the computing system might comprise at least one of customer premises equipment ("CPE"), universal CPE ("uCPE"), a software-defined wide area network ("SD-WAN") uCPE, a customer premises-based computing system, network interface device, or an optical network terminal, and/or the like. In some cases, the management console might comprise at least one of a controller of a healthcare data management system, a secure server computer, a distributed computing system, or a cloud computing system, and/or the like. In some instances, the one or more patient devices might each comprise at least one of one or more health monitoring devices, one or more thermometers, one or more drug delivery devices, one or more personal tracking devices, an insulin pump, a pace maker, one or more drug storage and dispensing devices, or one or more patient user devices, and/or the like. In some cases, the first patient data might comprise at least one of data regarding physiology of the patient, health tracking data of the patient, or data regarding a health alert associated with the patient, and/or the like.

According to some embodiments, the at least one healthcare data system might comprise at least one of an electronic medical record ("EMR") system, an electronic health record ("EHR") system, one or more healthcare servers, or one or more healthcare provider user devices. In some instances, the one or more healthcare providers might comprise at least one of a physician, a doctor, a surgeon, a nurse practitioner, a nurse, a medical assistant, a clinical receptionist, a pharmacist, a medical laboratory technician, a healthcare scheduler, or a health insurance agent, and/or the like. In some cases, the first network transport link might further comprise at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system is disposed, and/or the like.

In some embodiments, data segregation using a separate encryption key for each patient might be used over the first network transport link to ensure compliance with privacy and protection standards for medical or patient data. In some instances, sending the first patient data over the first network transport link to the at least one healthcare data system might comprise the first data collector publishing the first patient data via the computing system, and wherein the at least one healthcare data system subscribes to the first patient data.

According to some embodiments, the one or more patient devices might comprise at least one first patient device that is assigned to the first patient concurrent with the first data collector being assigned to the first patient, wherein the at least one first patient device might be pre-paired with the first data collector, enabling the at least one first patient device to automatically wirelessly communicate with the first data collector when both are activated at the first customer premises.

Alternatively, or additionally, the one or more patient devices might comprise at least one second patient device that is assigned to the first patient after the first data collector has been assigned to the first patient and has been collecting data from other patient devices among the one or more patient devices, wherein the at least one second patient device might each be added and registered as a new device that is associated with at least one of the first patient or the first data collector, enabling the at least one second patient device to automatically synchronize, and wirelessly communicate, with the first data collector when both are activated at the first customer premises.

In some embodiments, the method might further comprise establishing, with the computing system, a wireless link between the computing system and the first data collector, wherein the first patient data might be encrypted at each of the one or more patient devices, and wherein the first data collector might receive the first patient data that has been encrypted over a paired wireless link between the first data collector and each corresponding patient device among the one or more patient devices, wherein the first data collector might relay the collected first patient data to the computing system via the established wireless link. In some cases, the wireless link might comprise at least one of a Bluetooth wireless link, a WiFi wireless link, a ZigBee wireless link, or Z-wave wireless link, and/or the like. In some instances, the at least one first data collector might comprise a unique authentication token that is hard-coded.

According to some embodiments, the method might further comprise establishing, with the management console, a second network transport link between the management console and at least one of the computing system or the first data collector; and providing, with the management console, patient device data to the at least one of the computing system or the first data collector over the second network transport link. In some instances, the patient device data might comprise a list of authorized patient devices among the one or more patient devices that are associated with and assigned to the first patient. In some cases, providing the patient device data might comprise at least one of sending the patient device data to the computing system or providing the computing system with access over the second network transport link to a database containing the list of authorized patient devices associated with and assigned to the first patient. In some instances, the at least one of the computing system or the first data collector might prevent collection of data, or might prevent communication of data, from devices that are not listed in the patient device data. In some cases, the method might further comprise sending, with the management console, communications data to at least one patient device among the one or more patient devices via the computing system, wherein the communications data might comprise at least one of data regarding drug prescriptions for the patient, data regarding fitness regime, or data regarding diet, and/or the like.

In another aspect, a system might comprise a computing system and a management console. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive, from a first data collector, first patient data obtained by one or more patient devices that are associated with and assigned to a first patient, the first patient data being wirelessly collected from the one or more patient devices by the first data collector, the first data collector being assigned to the first patient, wherein the computing system and the first data collector are both located at a first customer premises associated with the first patient.

The management console might comprise at least one second processor and a second non-transitory computer readable medium communicatively coupled to the at least one second processor. The second non-transitory computer readable medium might have stored thereon computer software comprising a second set of instructions that, when executed by the at least one second processor, causes the management console to: establish a first network transport link between the computing system and at least one healthcare data system that is accessible by or associated with one or more healthcare providers; send the first patient data over the first network transport link to the at least one healthcare data system; and store the first patient data in the at least one healthcare data system, the first patient data being secured within a portion of the at least one healthcare data system that is allocated to information regarding the first patient, wherein the first network transport link is configured as a one-way network transport link that enables storage of the first patient data from the first data collector to the at least one healthcare data system while preventing access to any data stored in the at least one healthcare data system via the first network transport link.

According to some embodiments, the computing system might comprise at least one of customer premises equipment ("CPE"), universal CPE ("uCPE"), a software-defined wide area network ("SD-WAN") uCPE, a customer premises-based computing system, network interface device, or an optical network terminal, and/or the like. In some cases, the management console might comprise at least one of a controller of a healthcare data management system, a secure server computer, a distributed computing system, or a cloud computing system, and/or the like.

In some embodiments, the one or more patient devices might each comprise at least one of one or more health monitoring devices, one or more thermometers, one or more drug delivery devices, one or more personal tracking devices, an insulin pump, a pace maker, one or more drug storage and dispensing devices, or one or more patient user devices, and/or the like. In some instances, the at least one healthcare data system might comprise at least one of an electronic medical record ("EMR") system, an electronic health record ("EHR") system, one or more healthcare servers, or one or more healthcare provider user devices, and/or the like. In some cases, the one or more healthcare providers might comprise at least one of a physician, a doctor, a surgeon, a nurse practitioner, a nurse, a medical assistant, a clinical receptionist, a pharmacist, a medical laboratory technician, a healthcare scheduler, or a health insurance agent, and/or the like.

In yet another aspect, a method might comprise receiving, with a first data collector and from at least one patient device among one or more patient devices over a paired wireless link, first patient data obtained by the one or more patient devices, the first data collector and each of the one or more patient devices being associated with and assigned to a first patient, wherein the first data collector is located at a first customer premises associated with the first patient, wherein the first patient data is encrypted by each corresponding patient device among the at least one patient device prior to sending to the first data collector. The method might further comprise sending, with the first data collector, the first patient data to a computing system that is located at the first customer premises over a wireless link that has been established between the first data collector and the computing system, wherein the first patient data is subsequently sent over a first network transport link that has been established via one or more first networks between the computing system and at least one healthcare data system and stored in the at least one healthcare data system that is accessible by or associated with one or more healthcare providers, the first patient data being secured within a portion of the at least one healthcare data system that is allocated to information regarding the first patient, wherein the first network transport link is configured as a one-way network transport link that enables storage of the first patient data from the first data collector to the at least one healthcare data system while preventing access to any data stored in the at least one healthcare data system via the first network transport link.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-6 illustrate some of the features of the method, system, and apparatus for implementing health monitoring of patients, and, more particularly, to methods, systems, and apparatuses for implementing home health monitoring of patients via extension of healthcare system network into customer premises, as referred to above. The methods, systems, and apparatuses illustrated by FIGS. 1-6 refer to examples of different embodiments that include various components and steps, which can be considered alternatives or which can be used in conjunction with one another in the various embodiments. The description of the illustrated methods, systems, and apparatuses shown in FIGS. 1-6 is provided for purposes of illustration and should not be considered to limit the scope of the different embodiments.

With reference to the figures, FIG. 1 is a schematic diagram illustrating a system 100 for implementing home health monitoring of patients via extension of healthcare system network into customer premises, in accordance with various embodiments.

In the non-limiting embodiment of FIG. 1, system 100 might comprise a computing system 105 and corresponding database(s) 110. In some embodiments, computing system 105 might include, without limitation, at least one of customer premises equipment ("CPE"), universal CPE ("uCPE"), a software-defined wide area network ("SD-WAN") uCPE, a customer premises-based computing system, network interface device, or an optical network terminal, and/or the like. In some instances, database(s) 110 might be local to the computing system 105. In some cases, the database(s) 110 might be external, yet communicatively coupled, to the computing system 105. In other cases, the database(s) 110 might be integrated within the computing system 105.

System 100 might further comprise a data collector 115 and corresponding database 120. According to some embodiments, database 120 might be local to the data collector 115. In some cases, the database 120 might be external, yet communicatively coupled, to the data collector 115. In other cases, the database 120 might be integrated within the data collector 115. System 100 might further comprise one or more patient devices 125 that are associated with and assigned to a patient 130, each of the one or more patient devices 125 including, but not limited to, at least one of one or more health monitoring devices 125a, one or more (smart) thermometers 125b, one or more drug delivery devices 125c, one or more personal tracking devices 125d, an insulin pump 125e, a pace maker 125f, one or more drug storage and dispensing devices 125g, one or more patient user devices 125h, or one or more other patient devices 125i, and/or the like (collectively, "patient devices 125" or "doctor-prescribed devices 125" or the like).

In some cases, at least one of the one or more health monitoring devices 125a, the one or more personal tracking devices 125d, and/or the one or more other patient devices 125i might include, without limitation, at least one of a heart rate monitor, a pulse oximeter, an oximeter, a blood glucose monitor, a blood pressure monitor, a blood flow monitor, a nitrogen monitor, a carbon dioxide monitor, a sleep monitor, an activity monitor, a step counter, one or more limb movement monitors, one or more thermometers, one or more accelerometers, one or more gyroscopes, one or more body fat monitors, one or more body muscle monitors, one or more bone density monitors, one or more pH monitors, a body fluid monitor, an electroencephalograph, an electrocardiograph, a respiratory rate monitor, a serotonin monitor, an epilepsy monitor, a skin toxicity monitor, a blood toxicity monitor, an organ toxicity monitor, a cancer monitor, a blood tester, one or more blood alcohol level detectors, one or more drug testers, or one or more location monitors, and/or the like, and/or the like. The lightning bolt symbols are used to denote wireless communications between each patient device 125 and the data collector 115, and between the data collector 115 and the computing system 105.

According to some embodiments, the one or more patient devices 125 (e.g., the one or more health monitoring devices 125a, the one or more personal tracking devices 125d, and/or the one or more patient user devices 125h, or the like) might each comprise one or more first sensors that monitor physical conditions of a body of the patient 130 and/or one or more second sensors that monitor environmental conditions external to the body of the patient 130. In some cases, the one or more patient devices 125 might be a wearable device (e.g., health monitoring device(s) 125a, smart thermometer 125b, drug delivery device(s) 125c, personal tracking device(s) 125d, patient user device(s) 125h, etc.) that can be removably affixed to at least one of a portion of skin of the patient 130, a limb of the patient 130, an appendage of the patient 130, a torso of the patient 130, a head of the patient 130, or a piece of clothing worn by the patient 130, and/or the like. Alternatively, the one or more patient devices 125 might be an implantable device that can be at least one of implanted under one or more layers of skin of the patient 130 (e.g., health monitoring device(s) 125a, drug delivery device(s) 125c, insulin pump 125e, pace maker 125f, etc.), implanted within an organ of the patient 130 (e.g., health monitoring device(s) 125a, drug delivery device(s) 125c, pace maker 125f, etc.), implanted within a torso of the patient 130 (e.g., health monitoring device(s) 125a, drug delivery device(s) 125c, insulin pump 125, pace maker 125f, etc.), implanted in an internal cavity of the patient 130, or implanted in an external cavity of the patient 130, and/or the like. In some embodiments, multiple devices among the one or more patient devices 125 may be used to monitor the physiological conditions of the patient's body and/or to monitor the environmental conditions external to the patient's body, and can comprise either a plurality of wearable personal trackers, a plurality of implantable personal trackers, or a combination of at least one wearable personal tracker and at least one implantable personal tracker.

Herein, "personal tracker" or "personal tracking device" might refer to at least one of a fitness tracker, an activity tracker, or a medical monitor, and/or the like. The fitness tracker, activity tracker, and/or medical monitor might be worn by, or implanted in, any person or by a patient under the care of a physician or other healthcare provider. According to some embodiments, the one or more health monitoring devices 125a, the one or more drug delivery devices 125c, the one or more personal tracking devices 125d, the one or more patient user devices 125h, and/or the one or more other patient devices 125i might include, without limitation, at least one of a wearable drug delivery device, an implantable drug delivery device, a medical server, a medical database, a user device accessible by a physician, a user device accessible by a healthcare provider, a user device associated with the patient 130, a user device associated with a relative or guardian of the patient 130, a user device accessible by an emergency response team member, a smart medical alert bracelet, an Internet of Things ("IoT") human interface device (such as the IoT human interface device as described in detail in the '764 and '710 applications, which have already been incorporated herein by reference in their entirety), and/or the like.

In some embodiments, the one or more first sensors that monitor physical conditions of a body of the patient 130 might include, without limitation, at least one of a heart rate sensor, a pulse oximeter sensor, an oximeter sensor, a blood glucose sensor, a blood pressure sensor, a blood flow sensor, a nitrogen sensor, a carbon dioxide sensor, a sleep sensor, an activity sensor, a step counting sensor, one or more limb movement sensors, one or more temperature sensors, one or more accelerometer sensors, one or more gyroscopic sensors, one or more body fat sensors, one or more body muscle sensors, one or more bone density sensors, one or more pH sensors, a body fluid sensor, an electroencephalograph sensor, an electrocardiograph sensor, a respiratory rate sensor, a serotonin sensor, an epilepsy sensor, a skin toxicity sensor, a blood toxicity sensor, an organ toxicity sensor, a cancer sensor, a blood testing sensor, one or more blood alcohol level sensor, one or more drug testing sensor, or one or more location sensors, and/or the like.

According to some embodiments, the one or more second sensors that monitor environmental conditions external to the body of the patient 130 might include, but are not limited to, at least one of an ambient temperature sensor, a flame detector, a particulate sensor, a light sensor, a humidity sensor, an air quality sensor, an atmospheric oxygen level monitor, an atmospheric carbon dioxide level monitor, an atmospheric nitrogen level monitor, an atmospheric pressure sensor, an environmental carbon monoxide sensor, a smoke detector, a gas toxicity monitor, a carcinogen detector, a radiation sensor, a location sensor, a telecommunications signal sensor, a sound amplitude sensor, a frequency sensor, an accelerometer, a proximity sensor, a weather sensor, or a seismic sensor, and/or the like.

System 100 might further comprise a gateway device 135, which might include, without limitation, at least one of a residential gateway ("RG") device, a business gateway ("BG") device, a virtual gateway ("VG") device, a network interface device, an optical network terminal, a home Internet router, an Internet modem, or other gateway device, and/or the like. In some instances, the computing system 105 and corresponding database(s) 110, the data collector 115 and corresponding database 120, and the gateway device 135 may be located or disposed within a customer premises 140, which might include, but is not limited to, one of a single family house, a multi-dwelling unit ("MDU") within a multi-dwelling complex (including, but not limited to, an apartment building, an apartment complex, a condominium complex, a townhouse complex, a mixed-use building, etc.), a motel, an inn, a hotel, an office building or complex, a commercial building or complex, an industrial building or complex, and/or the like. The one or more patient devices 125 assigned to (and used to monitor) the patient 130 may be located or disposed at the customer premises 140, but may be designed or configured to be mobile, so as to monitor the patient 130 outside the customer premises 140. Although FIG. 1 depicts the computing system 105 and the gateway device 135 as distinct pieces of equipment, the various embodiments are not so limited, and the computing system 105 and the gateway device 135 either may be separate and interconnected devices within the customer premises 140 or may be integrated within a single device (not shown) within the customer premises 140.

In some embodiments, each of at least one first patient device 125 among the one or more patient devices 125 might be wirelessly paired, synced, or synchronized with the data collector 115. In some cases, where the at least one first patient device 125 is assigned to the patient 130 concurrent with the data collector 115 being assigned to the patient 130, the at least one first patient device 125 may be pre-paired with the data collector 115, enabling the at least one first patient device 125 to automatically wirelessly communicate with the data collector 115 when both are (simultaneously or concurrently) activated at the customer premises 140. Alternatively, where the at least one first patient device 125 is assigned to the patient 130 after the data collector 115 has been assigned to the patient 130 and has been collecting data from other patient devices 125 among the one or more patient devices 125, the at least one first patient device 125 may each be added and registered as a new device that is associated with at least one of the patient 130 or the data collector 115, enabling the at least one first patient device 125 to automatically synchronize, and wirelessly communicate, with the data collector 115 when both are (simultaneously or concurrently) activated at the customer premises 140.

System 100 might further comprise one or more networks 145, which might include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network(s) 145 might include an access network of the service provider (e.g., an Internet service provider ("ISP")). In another embodiment, the network(s) 145 might include a core network of the service provider, and/or the Internet.

System 100 might further comprise a management console 150 and corresponding database(s) 155. According to some embodiments, the management console 150 might include, but is not limited to, at least one of a controller of a healthcare data management system, a secure server computer, a distributed computing system, or a cloud computing system, and/or the like. In some instances, the management console 150 and corresponding database(s) 155 (e.g., management console 150a and corresponding database(s) 155a, or the like) might be part of or disposed within a healthcare system 160. Alternatively, or additionally, the management console 150 and corresponding database(s) 155 (e.g., management console 150b and corresponding database(s) 155b, or the like) might be disposed external to the healthcare system 160, in some cases, as part of at least one network 145 among the one or more networks 145 that is operated by a network, computing, and/or cloud service provider(s).

According to some embodiments, the healthcare system 160 might refer to at least one of a single healthcare facility, a collection of interconnected healthcare facilities (whether physically interconnected, connected via computing systems and wide area networks ("WAN"), and/or configured to securely communicate sensitive data with each other, or the like), a healthcare computing system, or a healthcare data network system, and/or the like. Healthcare system 160 might include, without limitation, one or more healthcare data systems 165 that may be accessible by or associated with one or more healthcare providers 170a-170n. In some embodiments, the one or more healthcare data systems 165 might include, without limitation, at least one of an electronic medical record ("EMR") system 165a, an electronic health record ("EHR") system 165b, one or more healthcare servers 165c, or one or more healthcare provider user devices 165d, and/or the like. In some instances, the one or more healthcare providers 170a-170n (collectively, "healthcare providers 170" or the like) might include, but are not limited to, at least one of a physician, a doctor, a surgeon, a nurse practitioner, a nurse, a medical assistant, a clinical receptionist, a pharmacist, a medical laboratory technician, a healthcare scheduler, or a health insurance agent, and/or the like.

Herein, "EMR" might refer to a digital version of a patient's chart, might contain the patient's medical and treatment history with a single healthcare provider, a single group of healthcare providers, or a single healthcare facility, and typically might not be shared with external healthcare providers or facilities. By contrast, "EHR" might refer to the patient's records from multiple healthcare providers, multiple groups of healthcare providers, or multiple healthcare facilities, might include the patient's personal information, the patient's demographics, test results, medical history, history of present illness, medications, allergies, immunization status, laboratory test results, radiology images, vital signs, billing information, and/or the like, and might follow the patient from healthcare provider/facility to healthcare provider/facility. Although FIG. 1 depicts a single patient's data collector 115 and patient device(s) 125 being communicatively coupled via computing system 105, gateway device 135, and network(s) 145 to management console 150a or 150b and to healthcare data system(s) 165, this is merely to simplify illustration, and the various embodiments are not so limited. Rather, management console 150a or 150b and healthcare data system(s) 165 are configured, and designed, to communicatively couple with one or more patient devices 125 assigned to each of a plurality of patients 130 who are located, or who reside, at geographically separate customer premises 140 (not limited to the same city, state/province, country, or region as the healthcare data system(s) 165).

In a non-limiting example, to properly assess the health of a patient 130, a healthcare provider 170 (e.g., a doctor, or the like) might hand out, assign, or prescribe one or more first patient devices 125 (and perhaps a data collector 115 as well) to the patient 130. The patient 130 would be asked to wear or attach the one or more first patient devices 125 on the patient's body or clothing (or to implant the one or more first patient devices 125 in the patient's body), the one or more first patient devices 125 being registered on a healthcare data system(s) 165 and/or the management console 150 as being associated with the patient 130. The management console 150 or the system might then extend the healthcare system network to each customer local area network in a customer premises 140 of the patient 130 among a plurality of customer local area networks in corresponding customer premises 140 associated with a corresponding plurality of patients 130, in the manner described below. In this way, patient privacy and security, as well as compliance with standards such as the standards set out in the health insurance portability and accountability act ("HIPAA") may be achieved.

That is, in operation, when the patient 130 returns to the patient's customer premises 140 with the assigned one or more first patient devices 125 (and, in some cases, the assigned data collector 115 as well), where the one or more first patient devices 125 are assigned to the patient 130 concurrent with the data collector 115 being assigned to the patient 130, the one or more first patient devices 125 may be pre-paired with the data collector 115, enabling the one or more first patient devices 125 to automatically wirelessly communicate with the data collector 115 when both are (simultaneously or concurrently) activated at the customer premises 140. Alternatively, where the one or more first patient devices 125 are assigned to the patient 130 after the data collector 115 has been assigned to the patient 130 and has been collecting data from other patient devices 125 among the one or more patient devices 125, the one or more first patient devices 125 may each be added and registered as a new device that is associated with at least one of the patient 130 or the data collector 115, enabling the one or more first patient devices 125 to automatically synchronize, and wirelessly communicate, with the data collector 115 when both are (simultaneously or concurrently) activated at the customer premises 140.

Once paired, the data collector 115 might establish a paired wireless link (depicted in FIG. 1 by lightning bolt symbols) between the data collector 115 and each of at least one patient device 125 among one or more patient devices 125 assigned to the patient 130. In some instances, the at least one data collector 115 might include, but is not limited to, a unique authentication token that is hard-coded in the at least one data collector 115. The data collector 115 might receive and collect first patient data from each of at least one patient device 125 among the one or more patient devices 125 over the corresponding paired wireless link. In some instances, the first patient data might include, but is not limited to, at least one of data regarding physiology of the patient, health tracking data of the patient, or data regarding a health alert associated with the patient, and/or the like. In some cases, the first patient data might be encrypted at each of the at least one patient device 125 prior to sending to the data collector 115. Computing system 105 might establish a wireless link (depicted in FIG. 1 by the lightning bolt symbol) between the computing system 105 and the data collector 115, which might relay the collected first patient data to the computing system 105 via the established wireless link. In some embodiments, the paired wireless link (between the data collector 115 and each of at least one patient device 125) and/or the wireless link (between the computing system 105 and the data collector 115) might each include, without limitation, at least one of a Bluetooth wireless link, a WiFi wireless link, a ZigBee wireless link, or Z-wave wireless link, and/or the like. The computing system 105 might receive, from the data collector 115, the first patient data obtained by at least one patient device 125 that is associated with and assigned to the patient 130.

At least one of the computing system 105 or the management console 150 might establish a first network transport link between the computing system 105 and at least one healthcare data system 165 (e.g., via the gateway device 135, network(s) 145, and the healthcare system 160, or the like) that is accessible by or associated with one or more healthcare providers 170a-170n. According to some embodiments, the first network transport link might include, without limitation, at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system 165 is disposed, and/or the like. At least one of the computing system 105 or the management console 150 might send the first patient data over the first network transport link to the at least one healthcare data system 165. The management console 150 might store the first patient data in the at least one healthcare data system 165, the first patient data being secured within a portion of the at least one healthcare data system 165 that is allocated to information regarding the patient 130 (such as shown and described in detail with respect to FIG. 3, or the like). In some embodiments, the first network transport link might be configured as a one-way network transport link that enables storage of the first patient data from the data collector 115 to the at least one healthcare data system 165 while preventing access to any data stored in the at least one healthcare data system 165 via the first network transport link.

In some embodiments, the management console 150 might establish a second network transport link between the management console 150 and at least one of the computing system 105 or the first data collector 115. In some cases, the second network transport link, like the first network transport link, might include, without limitation, at least one of a VPN, a SD-LAN, a SD-WAN, or a virtual extension of the healthcare provider network in which the at least one healthcare data system is disposed, and/or the like. In some instances, the management console 150 might provide patient device data to the at least one of the computing system 105 or the data collector 115 over the second network transport link, the patient device data comprising a list of authorized patient devices among the one or more patient devices 125 that are associated with and assigned to the patient 130. In some cases, providing the patient device data might comprise at least one of sending the patient device data to the computing system 105 or providing the computing system 105 with access over the second network transport link to a database (e.g., database(s) 155a or 155b, or the like) containing the list of authorized patient devices associated with and assigned to the patient. In some instances, the at least one of the computing system 105 or the data collector 115 might prevent collection of data, or prevent communication of data (to the computing system 105 and/or to the data collector 115), from devices that are not listed in the patient device data as being authorized. In some embodiments, the second network transport link and the first network transport link might be the same network transport link (e.g., as shown and described with respect to FIG. 2, or the like), while, in alternative embodiments, the second network transport link might be different or separate from the first network transport link (e.g., as shown and described with respect to FIG. 3, or the like). According to some embodiments, the management console 150 might send communications data to at least one patient device 125 among the one or more patient devices 125 via the computing system 105 over the second network transport link. In some instances, the communications data might include, without limitation, at least one of data regarding drug prescriptions for the patient, data regarding fitness regime, or data regarding diet, and/or the like.

During the monitoring period, a healthcare data system(s) 165 associated with a healthcare provider 170 (e.g., a doctor, or the like) might subscribe to data from each of the one or more patient devices 125 associated with (or registered to) the patient 130. Whether as a continuous monitor or as an event-based monitor (e.g., in response to sensors detecting when the patient's physiological condition worsens or when the patient suffers an injury, stroke, heart attack, or other serious condition, or the like), one or more patient devices 125 might publish sensor data associated with the health condition of the patient 130. In some embodiments, the sensor data might be published using conventional data routing techniques over conventional data networks for implementing publication/subscription of the sensor data. Alternatively, the sensor data might be published over prioritized data routing over message brokering system network for connected devices as described in detail in the '1566 application, the disclosure of which has already been incorporated herein by reference in its entirety for all purposes. In this way, whether utilizing the message brokering system, a conventional data network, or a conventional data routing system, the healthcare provider 170 can remotely monitor the health of the patient 130, and the one or more patient devices 125 can alert the healthcare provider 170 if sensors on the one or more patient devices 125 are triggered to send an alert message when the patient's physiological condition worsens or when the patient suffers an injury, stroke, heart attack, or other serious condition. By utilizing the message brokering system rather than using a conventional data network or conventional data routing system, the sensor data can be transported at a sustained maximum throughput (e.g., 4 Tbps or greater) across a highly distributed network without regard for network ownership.

Rather than just utilizing external health monitoring devices among the one or more patient devices 125, the healthcare provider 170 (e.g., the doctor, or the like) might surgically implant, hand out, or prescribe at least one of an insulin pump, a pacemaker, a drug delivery device (e.g., an implantable drug delivery device, a wearable drug delivery device, or the like), or a drug storage or dispensing device (e.g., a smart pill bottle, a smart pill case, or the like), and/or the like.

Alternatively, or additionally, the message brokering system of the '1566 application or other publish/subscribe ("pub/sub") messaging system (e.g., the conventional data network or the conventional data routing system, or the like) might be used to send data in the reverse direction, or along another identified path through the nodes of the system from the healthcare data system(s) 165 associated with the healthcare provider 170 to the one or more patient devices 125 associated with the patient 130, e.g., to update programming on the one or more patient devices 125, to pull sensor data from the one or more patient devices 125 in response to the healthcare provider's request, to update drug prescription for the drug delivery device(s) 125*c* or drug dispensing device(s) 125*g*, to adjust settings for the insulin pump 125*e* or pacemaker 125*f*, to send information (including, without limitation, at least one of data regarding drug prescriptions for the patient, data regarding fitness regime, or data regarding diet, and/or the like) to the patient 130 on a patient user device(s) 125*h* (e.g., a tablet computer, a smart phone, a mobile phone, a laptop computer, a desktop computer, a handheld medical communication device, etc.) of the patient 130, and/or the like.

In some aspects, the solution to conventional home health issues that arise from the need for home health workers to act as "data brokers" and the need to manually enter patient data into an EMR or an EHR associated with the patient comprises the following parts: (a) the management console (such as management console 150*a* or 150*b*, or the like); (b) the data collector (such as data collector 115, or the like); (c) the healthcare data system for capturing and storing the aggregated patient health data (e.g., the healthcare data system(s) 165, or the like); (d) the network transport (e.g., an Internet Protocol security ("IPsec") tunnel across an SD-WAN client, such as shown and described below with respect to FIGS. 2 and 3, or the like); and (e) the doctor-prescribed medical devices (such as patient devices 125, or the like).

In some embodiments, the management console might be a web-based management console, or the like. In some cases, the management console might perform one or more of the following functions: (1) register patients; (2) register patient devices; (3) assign patient devices to patients; (4) configure the SD-WAN; (5) configure the data collector; (6) download the raw health data for a doctor or other healthcare provider (in some cases, via an application programming interface ("API") or the like); and/or (7) integrate downloaded health data into the healthcare data system(s) 165 (e.g., into an EMR or into an EHR, or the like).

According to some embodiments, when the data collector is assigned to a patient, the data collector is provided (by the management console) with a unique authentication token for replicating patient device data, and the Bluetooth addresses for the authorized patient devices are automatically registered in the software (e.g., software application ("app") or data collector controller system, or the like). The data collector is configured to only accept patient devices that have been authorized and registered. In some instances, the data collector might comprise a lite database structure that is fed from the management console so that additional devices can be assigned to the patient. In some cases, the data collector might run a database instance (e.g., Harper DB instance, or the like) that natively replicates a database instance (e.g., Harper DB instance, or the like) running on a server or healthcare data system in the healthcare system (e.g., at a healthcare facility or the like), or the like.

In some embodiments, the healthcare data system might be a large data store or analytical database. Data may be replicated from the data collector directly into the data store. Data within the data store is encrypted with a separate encryption key for each patient. In some cases, data in the data store may be able to be downloaded in composite form by day, week, month, quarter, year, decade, and/or the like.

According to some embodiments, the network transport might utilize an SD-WAN client that is ARM-based or based on other reduced instruction set computing ("RISC") architecture for computer processors. The SD-WAN provides a logical method for extending the hospital or healthcare network, similar to a multi-point VPN or the like, but only for inbound data, and only for data flowing into the analytical data store. HIPAA security and privacy rules compliance may be accomplished through the use of data segregation (e.g., using separate encryption keys for different patients and their file or data, etc.) and through the use of IPsec VPN to provide data protection during transfer of data (or mirroring of data) from the data collector to the analytical data store. All access to the data may be logged via the data store natively.

In some embodiments, the patient devices may be auto-paired with the data collector. In some instances, the data collector might utilize a python-based application that reads in the authorized devices from an encrypted database that can only be updated by the management console. The patient devices might have an assigned Bluetooth address (in some cases, hardwired into the Bluetooth radio in each patient device). The patient devices may be added or removed from the management console.

These and other functions of the system 100 (and its components) are described in greater detail below with respect to FIGS. 2-4.

Figure 2:
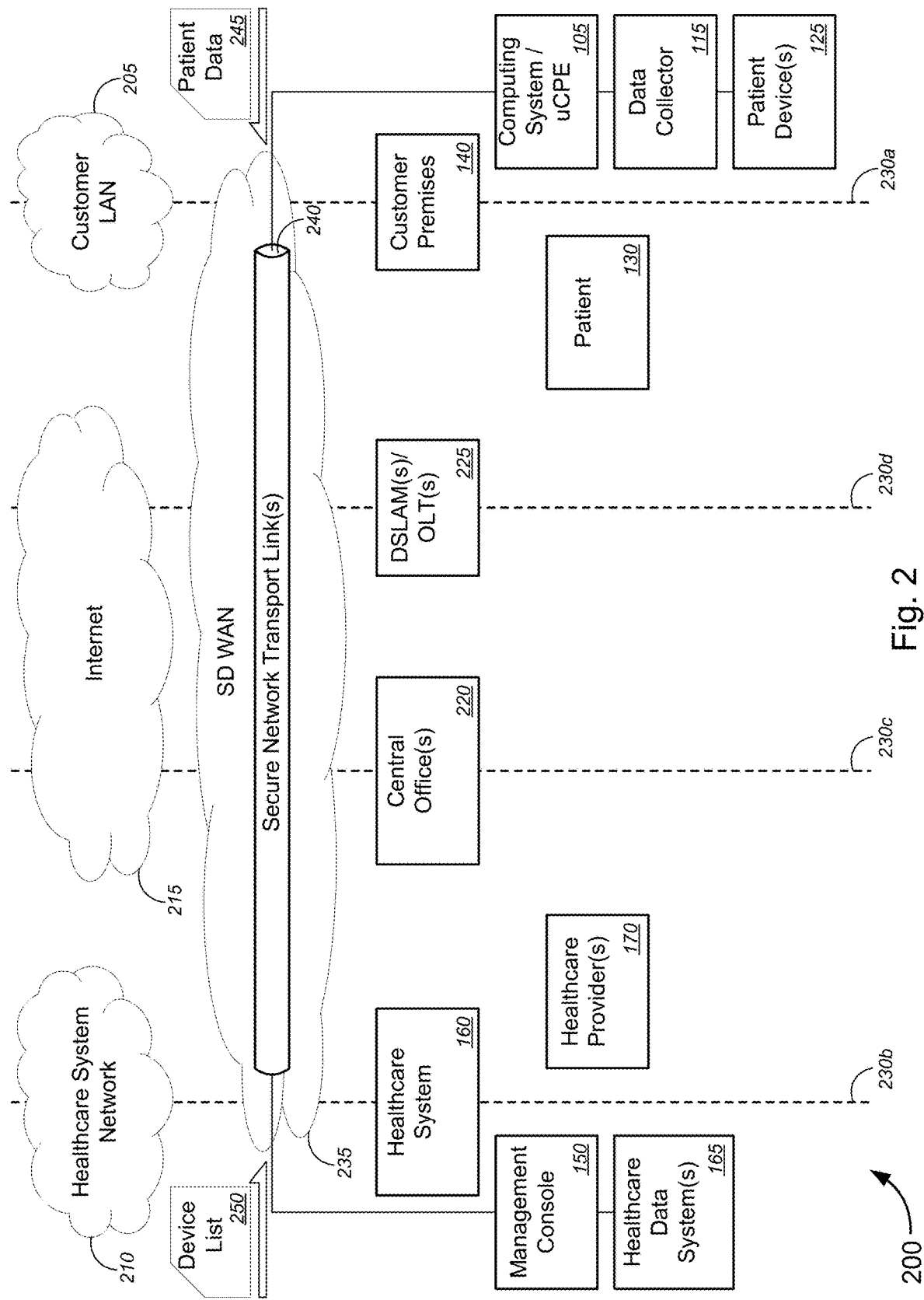
FIG. 2 is a schematic diagram illustrating a non-limiting example of extension of a software defined wide area network ("SD-WAN") to extend a healthcare system network into the customer premises for implementing home health monitoring of patients, in accordance with various embodiments.

FIG. 2 is a schematic diagram illustrating a non-limiting example 200 of extension of a software defined wide area network ("SD-WAN") to extend a healthcare system network into the customer premises for implementing home health monitoring of patients, in accordance with various embodiments. Components of FIG. 2 having the same or similar reference numeral(s) as components of FIG. 1 are as described in detail above with respect to FIG. 1.

In the non-limiting embodiment of FIG. 2, system 200 might comprise a customer local area network ("LAN") 205 located at customer premises 140 (as indicated by the dashed line 230a), a healthcare system network 210 located at a healthcare system 160 (as indicated by the dashed line 230b), the Internet 215 or other network(s) (similar to network(s) 145, or the like) spanning or extending over one or more central offices 220 and/or one or more digital subscriber line access multiplexers ("DSLAMs") or one or more optical line terminals ("OLTs") 225 (as indicated by the dashed lines 230c and 230d), and/or the like.

Similar to the examples as described above with respect to FIG. 1, in a non-limiting example, to properly assess the health of a patient 130, a healthcare provider 170 (e.g., a doctor, or the like) might hand out, assign, or prescribe one or more first patient devices 125 (and perhaps a data collector 115 as well) to the patient 130. The patient 130 would be asked to wear or attach the one or more first patient devices 125 on the patient's body or clothing (or to implant the one or more first patient devices 125 in the patient's body), the one or more first patient devices 125 being registered on a healthcare data system(s) 165 and/or the management console 150 as being associated with the patient 130. The management console 150 or the system then might establish or might extend the healthcare system network 210 to each customer LAN 205 in a customer premises 140 of the patient 130 among a plurality of such patients 130, in the manner described below, by extending a software defined wide area network ("SD-WAN") 235 from the healthcare system network 210 over the Internet 215 into the customer LAN 205. In this way, patient privacy and security, as well as compliance with standards such as the standards set out in the health insurance portability and accountability act ("HIPAA") may be achieved.

That is, in operation, when the patient 130 returns to the patient's customer premises 140 with the assigned one or more first patient devices 125 (and, in some cases, the assigned data collector 115 as well), where the one or more first patient devices 125 are assigned to the patient 130 concurrent with the data collector 115 being assigned to the patient 130, the one or more first patient devices 125 may be pre-paired with the data collector 115, enabling the one or more first patient devices 125 to automatically wirelessly communicate with the data collector 115 when both are (simultaneously or concurrently) activated at the customer premises 140. Alternatively, where the one or more first patient devices 125 are assigned to the patient 130 after the data collector 115 has been assigned to the patient 130 and has been collecting data from other patient devices 125 among the one or more patient devices 125, the one or more first patient devices 125 may each be added and registered as a new device that is associated with at least one of the patient 130 or the data collector 115, enabling the one or more first patient devices 125 to automatically synchronize, and wirelessly communicate, with the data collector 115 when both are (simultaneously or concurrently) activated at the customer premises 140.

Once paired, the data collector 115 might establish a paired wireless link (depicted in FIG. 2 by a solid line) between the data collector 115 and each of at least one patient device 125 among one or more patient devices 125 assigned to the patient 130. In some instances, the at least one data collector 115 might include, but is not limited to, a unique authentication token that is hard-coded in the at least one data collector 115. The data collector 115 might receive and collect first patient data 245 from each of at least one patient device 125 among the one or more patient devices 125 over the corresponding paired wireless link. In some instances, the first patient data 245 might include, but is not limited to, at least one of data regarding physiology of the patient, health tracking data of the patient, or data regarding a health alert associated with the patient, and/or the like. In some cases, the first patient data 245 might be encrypted at each of the at least one patient device 125 prior to sending to the data collector 115. Computing system 105 might establish a wireless link (depicted in FIG. 2 by a solid line) between the computing system 105 and the data collector 115, which might relay the collected first patient data 245 to the computing system 105 via the established wireless link. In some embodiments, the paired wireless link (between the data collector 115 and each of at least one patient device 125) and/or the wireless link (between the computing system 105 and the data collector 115) might each include, without limitation, at least one of a Bluetooth wireless link, a WiFi wireless link, a ZigBee wireless link, or Z-wave wireless link, and/or the like. The computing system 105 might receive, from the data collector 115, the first patient data 245 obtained by at least one patient device 125 that is associated with and assigned to the patient 130.

At least one of the computing system 105 or the management console 150 might establish a first network transport link 240 between the computing system 105 and at least one healthcare data system 165 (e.g., via the SD-WAN 235 and via management console 150, or the like) that is accessible by or associated with one or more healthcare providers 170. According to some embodiments, the first network transport link 240 might include, without limitation, at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network 210 in which the at least one healthcare data system 165 is disposed, and/or the like. At least one of the computing system 105 or the management console 150 might send the first patient data 245 over the first network transport link 240 to the at least one healthcare data system 165. The management console 150 might store the first patient data 245 in the at least one healthcare data system 165, the first patient data 245 being secured within a portion of the at least one healthcare data system 165 that is allocated to information regarding the patient 130 (such as shown and described in detail with respect to FIG. 3, or the like). In some embodiments, the first network transport link 240 might be configured as a one-way network transport link that enables storage of the first patient data 245 from the data collector 115 to the at least one healthcare data system 165 while preventing access to any data stored in the at least one healthcare data system 165 via the first network transport link. According to some embodiments, data segregation using a separate encryption key for each patient may be used over the first network transport link(s) 240 to ensure compliance with privacy and protection standards for medical or patient data.

In some embodiments, the management console 150 might establish a second network transport link between the management console 150 and at least one of the computing system 105 or the first data collector 115. In some cases, the second network transport link, like the first network transport link, might include, without limitation, at least one of a VPN, a SD-LAN, a SD-WAN, or a virtual extension of the healthcare provider network in which the at least one healthcare data system is disposed, and/or the like. In some instances, the management console 150 might provide patient device data or patient device list 250 to the at least one of the computing system 105 or the data collector 115 over the second network transport link, the patient device data or patient device list 250 comprising a list of authorized patient devices among the one or more patient devices 125 that are associated with and assigned to the patient 130. In some cases, providing the patient device data or patient device list 250 might comprise at least one of sending the patient device data or patient device list 250 to the computing system 105 or providing the computing system 105 with access over the second network transport link to a database (e.g., database(s) 155a or 155b, or the like) containing the list of authorized patient devices associated with and assigned to the patient. In some instances, the at least one of the computing system 105 or the data collector 115 might prevent collection of data, or prevent communication of data (to the computing system 105 and/or to the data collector 115), from devices that are not listed in the patient device data or patient device list 250 as being authorized. In some embodiments, the second network transport link and the first network transport link 240 might be the same network transport link 240 (e.g., as shown in FIG. 2, or the like), while, in alternative embodiments, the second network transport link might be different or separate from the first network transport link 240 (e.g., as shown and described with respect to FIG. 3, or the like). According to some embodiments, the management console 150 might send communications data to at least one patient device 125 among the one or more patient devices 125 via the computing system 105 over the second network transport link. In some instances, the communications data might include, without limitation, at least one of data regarding drug prescriptions for the patient, data regarding fitness regime, or data regarding diet, and/or the like.

During the monitoring period, a healthcare data system(s) 165 associated with a healthcare provider 170 (e.g., a doctor, or the like) might subscribe to data from each of the one or more patient devices 125 associated with (or registered to) the patient 130. Whether as a continuous monitor or as an event-based monitor (e.g., in response to sensors detecting when the patient's physiological condition worsens or when the patient suffers an injury, stroke, heart attack, or other serious condition, or the like), one or more patient devices 125 might publish sensor data associated with the health condition of the patient 130. In some embodiments, the sensor data might be published using conventional data routing techniques over conventional data networks for implementing publication/subscription of the sensor data. Alternatively, the sensor data might be published (as patient data 245) over prioritized data routing over message brokering system network for connected devices as described in detail in the '1566 application, the disclosure of which has already been incorporated herein by reference in its entirety for all purposes. In this way, whether utilizing the message brokering system, a conventional data network, or a conventional data routing system, the healthcare provider 170 can remotely monitor the health of the patient 130, and the one or more patient devices 125 can alert the healthcare provider 170 if sensors on the one or more patient devices 125 are triggered to send an alert message when the patient's physiological condition worsens or when the patient suffers an injury, stroke, heart attack, or other serious condition. By utilizing the message brokering system rather than using a conventional data network or conventional data routing system, the sensor data can be transported at a sustained maximum throughput (e.g., 4 Tbps or greater) across a highly distributed network without regard for network ownership.

Rather than just utilizing external health monitoring devices among the one or more patient devices 125, the healthcare provider 170 (e.g., the doctor, or the like) might surgically implant, hand out, or prescribe at least one of an insulin pump, a pacemaker, a drug delivery device (e.g., an implantable drug delivery device, a wearable drug delivery device, or the like), or a drug storage or dispensing device (e.g., a smart pill bottle, a smart pill case, or the like), and/or the like.

Alternatively, or additionally, the message brokering system of the '1566 application or other publish/subscribe ("pub/sub") messaging system (e.g., the conventional data network or the conventional data routing system, or the like) might be used to send data in the reverse direction, or along another identified path through the nodes of the system from the healthcare data system(s) 165 associated with the healthcare provider 170 to the one or more patient devices 125 associated with the patient 130, e.g., to update programming on the one or more patient devices 125, to pull sensor data (such as patient data 245) from the one or more patient devices 125 in response to the healthcare provider's request, to update drug prescription for the drug delivery device(s) or drug dispensing device(s), to adjust settings for the insulin pump or pacemaker, to send information (including, without limitation, at least one of data regarding drug prescriptions for the patient, data regarding fitness regime, or data regarding diet, and/or the like) to the patient 130 on a patient user device(s) (e.g., a tablet computer, a smart phone, a mobile phone, a laptop computer, a desktop computer, a handheld medical communication device, etc.) of the patient 130, and/or the like.

Figure 3:
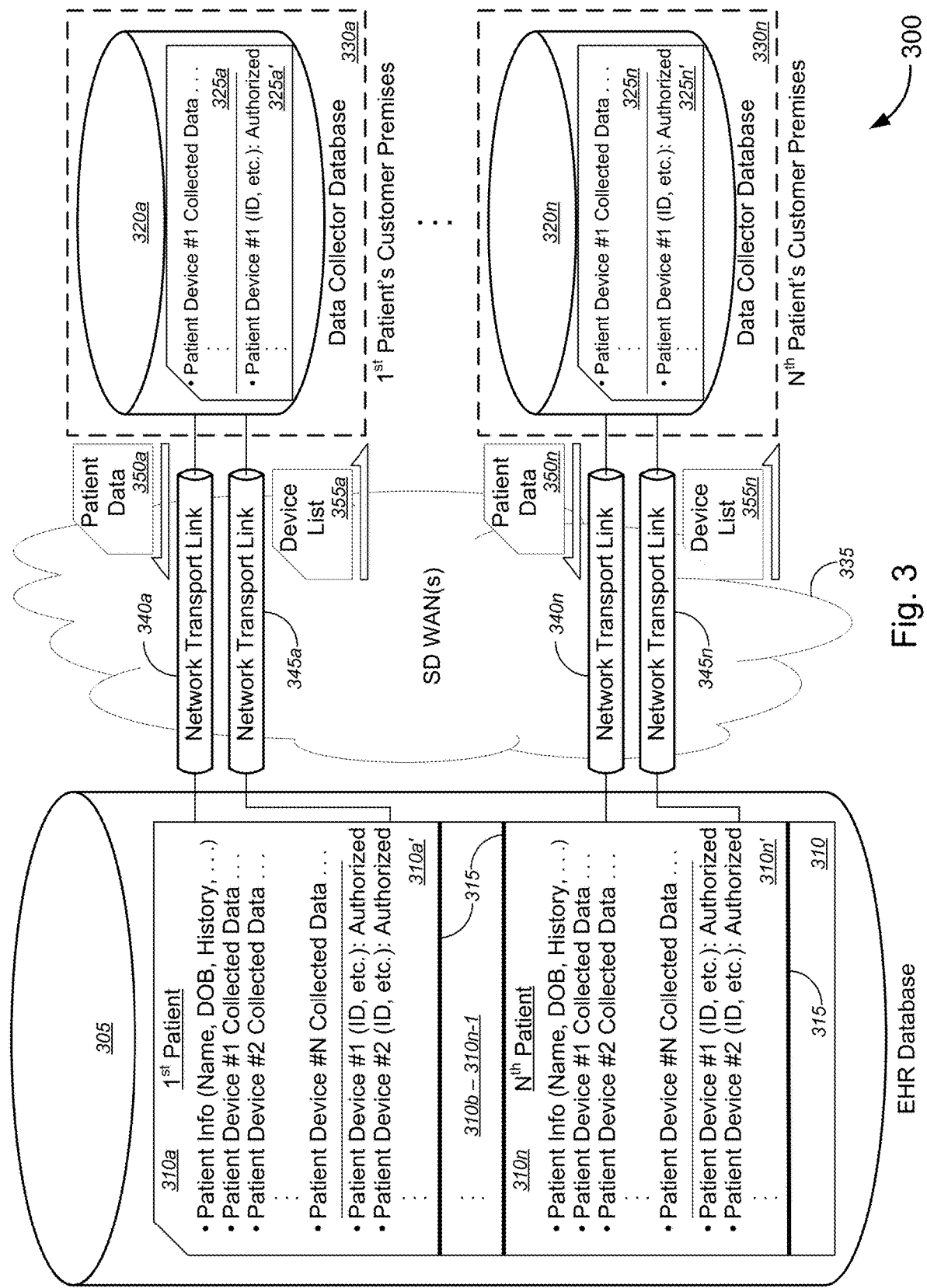
FIG. 3 is a schematic diagram illustrating a non-limiting example of mirroring of data in healthcare system database and in data collector database via secure network transport links and segregation of patient data in the healthcare system database for a plurality of patients, in accordance with various embodiments.

FIG. 3 is a schematic diagram illustrating a non-limiting example 300 of mirroring of data in healthcare system database and in data collector database via secure network transport links and segregation of patient data in the healthcare system database for a plurality of patients, in accordance with various embodiments.

In the non-limiting embodiment of FIG. 3, system 300 might comprise a healthcare data system (such as electronic health record ("EHR") database 305, or the like), which might comprise a secure and segmented data store 310, or the like. In some embodiments, the secure and segmented data store 310 might include, without limitation, a first portion 310a associated with a first patient through an $N^{th}$ portion 310n associated with an $N^{th}$ patient, a first sub-portion 310a' associated with patient devices associated with or assigned to the first patient through an $N^{th}$ sub-portion 310n' associated with patient devices associated with or assigned to the $N^{th}$ patient, and one or more partitions or data segmentation mechanisms (depicted in FIG. 3 by dark solid lines 315, or the like), and/or the like. The one or more partitions or data segmentation mechanisms ensure secure separation of data (as well as restricted transfer of access to data) between or among data associated with different patients in a manner that is compliant with standards such as the standards set out in the health insurance portability and accountability act ("HIPAA"), or the like. System 300 might further comprise a first data collector database 320a (similar to database 120 of FIG. 1, or the like) disposed at the customer premises 330a associated with the first patient—in some cases, external, yet communicatively coupled with a data collector (similar to data collector 115 of FIG. 1, or the like) that has been assigned to the first patient; while, in other cases, integrated with said data collector. Similarly, System 300 might further comprise a plurality of data collector databases 320 through an $N^{th}$ data collector database 320n (similar to database 120 of FIG. 1, or the like) that is disposed at the customer premises 330n associated with the $N^{th}$ patient—in some cases, external, yet communicatively coupled with a data collector (similar to data collector 115 of FIG. 1, or the like) that has been assigned to the $N^{th}$ patient; while, in other cases, integrated with said data collector.

System 300 might further comprise one or more software defined wide area networks ("SD-WANs") 335, a plurality of first network transport links 340a-340n, and a plurality of second network transport links 345a-345n, and/or the like. The one or more SD-WANs 335, the plurality of first network transport links 340a-340n, and the plurality of second network transport links 345a-345n may be established by the management console 150 as described above with respect to FIGS. 1 and 2. The plurality of first network transport links 340a-340n (which might each include, without limitation, a virtual private network ("VPN") or an Internet Protocol security ("IPsec") tunnel in the one or more SD-WANs 335, and/or the like) may each be established, by the management console 150 (shown in FIGS. 1 and 2, or the like), between the healthcare data system (in this case, the EHR database 305) and the corresponding data collector (or, in this case, the corresponding data collector database among the data collector databases 330a-330n associated with the plurality of patients), via the SD-WAN(s) 335, and may be used to securely transfer, transmit/receive, copy, and/or mirror patient device collected data (as patient data 350a-350n) that is collected and stored in a first portion (e.g., database portions 325a-325n) of each of the data collector databases 320a-320n associated with the plurality of patients onto corresponding portions 310a-310n of the secure and segmented data store 310 of the EHR database 305. Similarly, the plurality of second network transport links 345a-345n may each be established, by the management console 150 (shown in FIGS. 1 and 2, or the like), between the healthcare data system (in this case, the EHR database 305) and the corresponding data collector (or, in this case, the corresponding data collector database among the data collector databases 330a-330n associated with the plurality of patients), via the SD-WAN(s) 335, and may be used to securely transfer, transmit/receive, copy, and/or mirror a list(s) of authorized patient devices (as device list 355a-355n) that is stored in first through $N^{th}$ sub-portions 310a'-310n' of the secure and segmented data store 310 of the EHR database 305 onto corresponding second portions (e.g., database portions 325a'-325n') of each of the data collector databases 320a-320n associated with the plurality of patients. In some embodiments, each of the first network transport links 340a-340n might be configured as a one-way network transport link that enables storage of the patient data 350a-350n from the corresponding data collector (or data collector database among the data collector databases 320a-320n) to the at least one healthcare data system (in particular, corresponding one of the first through $N^{th}$ portions 310a-310n of the secure and segmented data store 310 of the EHR database 305, while preventing access to any data stored in the at least one healthcare data system via the first network transport link(s) 340a-340n. According to some embodiments, data segregation using a separate encryption key for each patient may be used over the first network transport links 340a-340n to ensure compliance with privacy and protection standards for medical or patient data. Similar data segregation techniques may be used for the second network transport links (345a-345n; if different from the first network transport links 340a-340n) to ensure that the list of authorized devices (i.e., device list 355a-355n) are not compromised, thereby preventing unauthorized or unknown devices from being maliciously, surreptitiously, and/or unwantedly added as authorized devices, which would provide a point(s) of vulnerability to the collected patient data 350a-350n (whether at the EHR database 305 and/or at one or more of the data collector databases 320a-320n, or the like).

For example, the management console 150 (shown in FIGS. 1 and 2, or the like) may establish a first network transport links 340a between the healthcare data system (in this case, the EHR database 305) and a data collector (or, in this case, a data collector database 330a) that is associated with a first patient, via the SD-WAN(s) 335, and may be used to securely transfer, transmit/receive, copy, and/or mirror patient device collected data (as patient data 350a, including, but not limited to, patient device #1 collected data through patient device #N collected data, or the like) that is collected and stored in a first portion (e.g., database portion 325a) of the data collector database 320a associated with the first patient onto the first portion 310a of the secure and segmented data store 310 of the EHR database 305. In a similar manner, the management console 150 (shown in FIGS. 1 and 2, or the like) may establish a second network transport link 345a (which might each include, without limitation, a VPN or an IPsec tunnel in the one or more SD-WANs 335, and/or the like) between the healthcare data system (in this case, the EHR database 305) and the data collector (or, in this case, the data collector database 330a) that is associated with the first patient, via the SD-WAN(s) 335, and may be used to securely transfer, transmit/receive, copy, and/or mirror a list(s) of authorized patient devices (as device list 355a, including, without limitation, at least one of identification data associated with each of patient devices #1 through #N, a notation associated with each patient device indicating whether that patient device is an authorized device, or a notation associated with each patient device indicating whether that patient device is an unknown or unauthorized device, and/or the like) that is stored in the first sub-portion 310a' of the secure and segmented data store 310 of the EHR database 305 onto a second portion (e.g., database portion 325a') of the data collector database 320a associated with the first patient.

Likewise, the management console 150 (shown in FIGS. 1 and 2, or the like) may establish a first network transport links 340n between the healthcare data system (in this case, the EHR database 305) and a data collector (or, in this case, a data collector database 330n) that is associated with an $N^{th}$ patient, via the SD-WAN(s) 335, and may be used to securely transfer, transmit/receive, copy, and/or mirror patient device collected data (as patient data 350n, including, but not limited to, patient device #1 collected data through patient device #N collected data, or the like) that is collected and stored in a first portion (e.g., database portion 325n) of the data collector database 320n associated with the $N^{th}$ patient onto the $N^{th}$ portion 310n of the secure and segmented data store 310 of the EHR database 305. In a similar manner, the management console 150 (shown in FIGS. 1 and 2, or the like) may establish a second network transport link 345n between the healthcare data system (in this case, the EHR database 305) and the data collector (or, in this case, the data collector database 330n) that is associated with the $N^{th}$ patient, via the SD-WAN(s) 335, and may be used to securely transfer, transmit/receive, copy, and/or mirror a list(s) of authorized patient devices (as device list 355n, including, without limitation, at least one of identification data associated with each of patient devices #1 through #N, a notation associated with each patient device indicating whether that patient device is an authorized device, or a notation associated with each patient device indicating whether that patient device is an unknown or unauthorized device, and/or the like) that is stored in the $N^{th}$ sub-portion 310n' of the secure and segmented data store 310 of the EHR database 305 onto a second portion (e.g., database portion 325n') of the data collector database 320n associated with the $N^{th}$ patient.

Figure 4A:
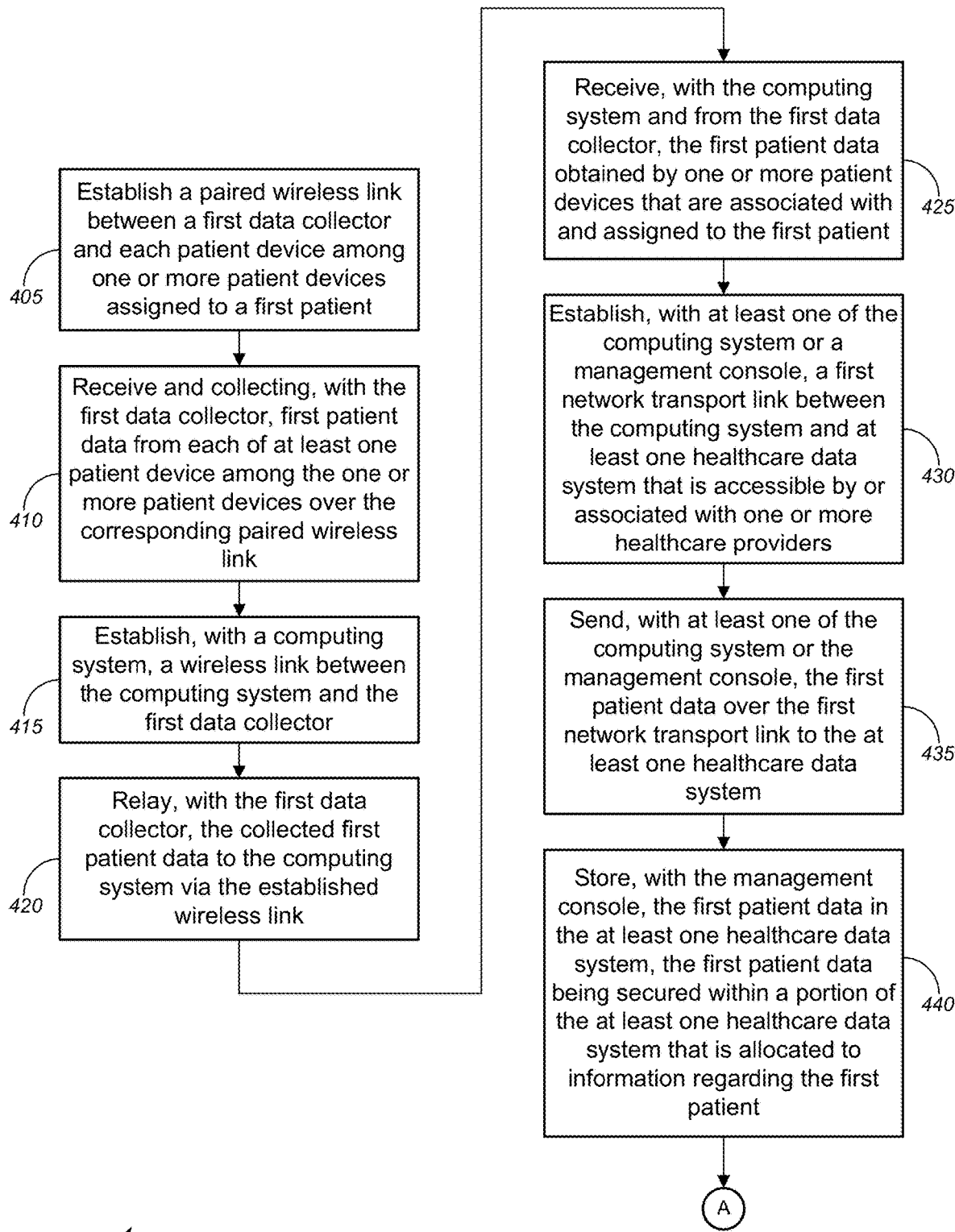
FIGS. 4A and 4B are flow diagrams illustrating a method for implementing home health monitoring of patients via extension of healthcare system network into customer premises, in accordance with various embodiments.
Figure 4B:
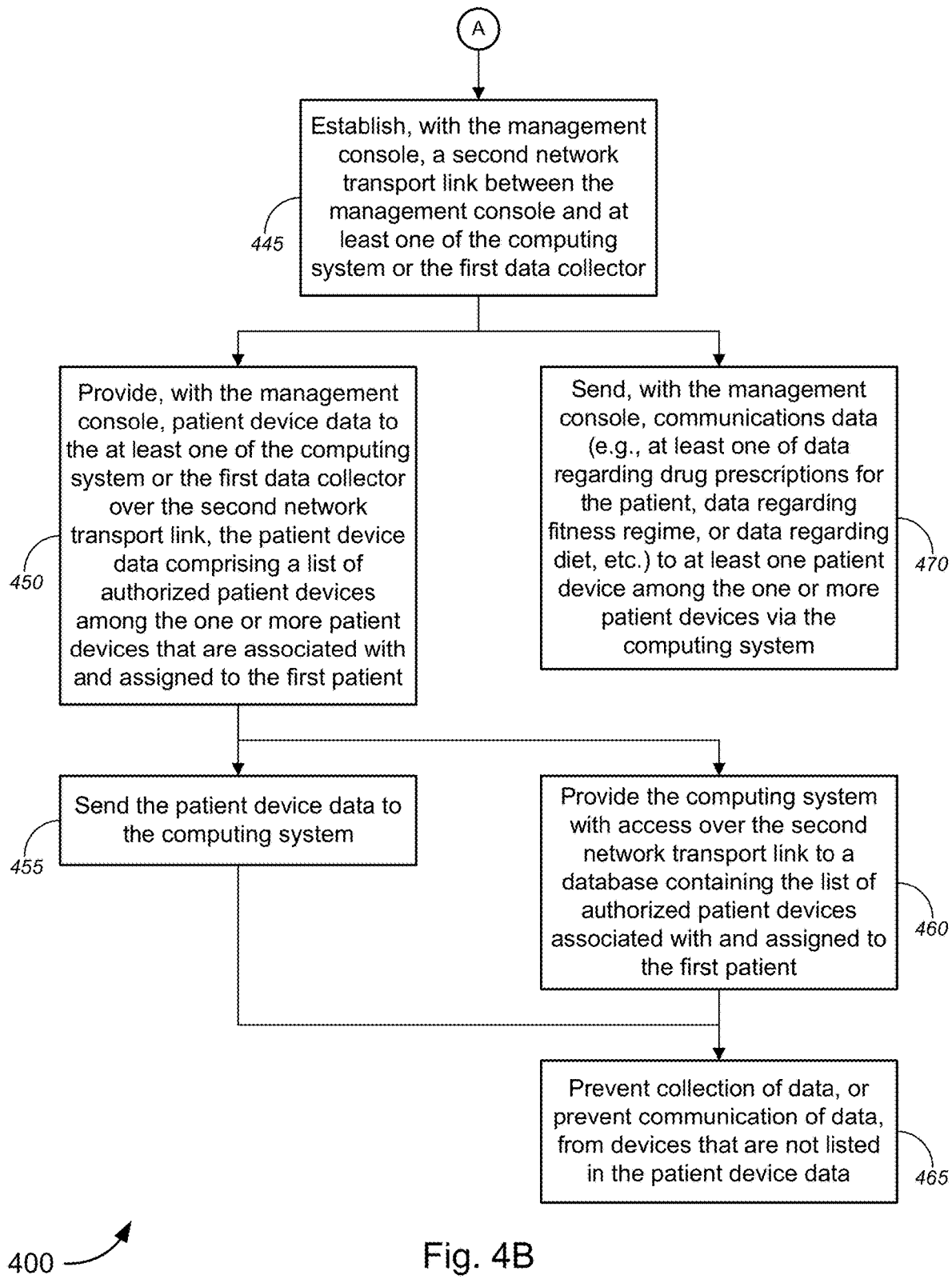

FIGS. 4A and 4B (collectively, "FIG. 4") are flow diagrams illustrating a method 400 for implementing home health monitoring of patients via extension of healthcare system network into customer premises, in accordance with various embodiments. Method 400 of FIG. 4A continues onto FIG. 4B following the circular marker denoted, "A."

While the techniques and procedures are depicted and/or described in a certain order for purposes of illustration, it should be appreciated that certain procedures may be reordered and/or omitted within the scope of various embodiments. Moreover, while the method 400 illustrated by FIG. 4 can be implemented by or with (and, in some cases, are described below with respect to) the systems, examples, or embodiments 100, 200, and 300 of FIGS. 1, 2, and 3, respectively (or components thereof), such methods may also be implemented using any suitable hardware (or software) implementation. Similarly, while each of the systems, examples, or embodiments 100, 200, and 300 of FIGS. 1, 2, and 3, respectively (or components thereof), can operate according to the method 400 illustrated by FIG. 4 (e.g., by executing instructions embodied on a computer readable medium), the systems, examples, or embodiments 100, 200, and 300 of FIGS. 1, 2, and 3 can each also operate according to other modes of operation and/or perform other suitable procedures.

In the non-limiting embodiment of FIG. 4A, method 400, at block 405, might comprise establishing a paired wireless link between a first data collector and each patient device among one or more patient devices assigned to a first patient. At block 410, method 400 might comprise receiving and collecting, with the first data collector, first patient data from each of at least one patient device among the one or more patient devices over the corresponding paired wireless link. Method 400 might further comprise establishing, with a computing system, a wireless link between the computing system and the first data collector (block 415) and relaying, with the first data collector, the collected first patient data to the computing system via the established wireless link (block 420). In some embodiments, the wireless link might include, without limitation, at least one of a Bluetooth wireless link, a WiFi wireless link, a ZigBee wireless link, or Z-wave wireless link, and/or the like.

At block 425, method 400 might comprise receiving, with the computing system and from the first data collector, the first patient data obtained by one or more patient devices that are associated with and assigned to the first patient. In some instances, the at least one first data collector might include, but is not limited to, a unique authentication token that is hard-coded in the at least one first data collector. Method 400 might further comprise, at block 430, establishing, with at least one of the computing system or a management console, a first network transport link between the computing system and at least one healthcare data system that is accessible by or associated with one or more healthcare providers. Method 400, at block 435, might comprise sending, with at least one of the computing system or the management console, the first patient data over the first network transport link to the at least one healthcare data system. Method 400 might further comprise storing, with the management console, the first patient data in the at least one healthcare data system, the first patient data being secured within a portion of the at least one healthcare data system that is allocated to information regarding the first patient (block 440). In some embodiments, the first network transport link might be configured as a one-way network transport link that enables storage of the first patient data from the first data collector to the at least one healthcare data system while preventing access to any data stored in the at least one healthcare data system via the first network transport link.

According to some embodiments, the computing system might include, without limitation, at least one of customer premises equipment ("CPE"), universal CPE ("uCPE"), a software-defined wide area network ("SD-WAN") uCPE, a customer premises-based computing system, network interface device, or an optical network terminal, and/or the like. In some instances, the management console might include, but is not limited to, at least one of a controller of a healthcare data management system, a secure server computer, a distributed computing system, or a cloud computing system, and/or the like. In some cases, the one or more patient devices might each include, without limitation, at least one of one or more health monitoring devices, one or more thermometers, one or more drug delivery devices, one or more personal tracking devices, an insulin pump, a pace maker, one or more drug storage and dispensing devices, or one or more patient user devices, and/or the like. In some instances, the first patient data might include, but is not limited to, at least one of data regarding physiology of the patient, health tracking data of the patient, or data regarding a health alert associated with the patient, and/or the like.

In some embodiments, the at least one healthcare data system might include, without limitation, at least one of an electronic medical record ("EMR") system, an electronic health record ("EHR") system, one or more healthcare servers, or one or more healthcare provider user devices, and/or the like. In some instances, the one or more healthcare providers might include, but are not limited to, at least one of a physician, a doctor, a surgeon, a nurse practitioner, a nurse, a medical assistant, a clinical receptionist, a pharmacist, a medical laboratory technician, a healthcare scheduler, or a health insurance agent, and/or the like. In some instances, the first network transport link might further include, without limitation, at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system is disposed, and/or the like.

Method 400 might continue onto the process at optional block 445 in FIG. 4B following the circular marker denoted, "A."

At optional block 445 in FIG. 4B (following the circular marker denoted, "A"), method 400 might comprise establishing, with the management console, a second network transport link between the management console and at least one of the computing system or the first data collector. Method 400 either might continue onto the process at block 450 and/or might continue onto the process at block 470.

At block 450, method 400 might comprise providing, with the management console, patient device data to the at least one of the computing system or the first data collector over the second network transport link, the patient device data comprising a list of authorized patient devices among the one or more patient devices that are associated with and assigned to the first patient. In some embodiments, providing the patient device data might comprise at least one of: sending the patient device data to the computing system (block 455); or providing the computing system with access over the second network transport link to a database containing the list of authorized patient devices associated with and assigned to the first patient (block 460). Method 400 might further comprise preventing collection of data, or preventing communication of data, from devices that are not listed in the patient device data.

At block 470, method 400 might comprise sending, with the management console, communications data to at least one patient device among the one or more patient devices via the computing system. In some instances, the communications data might include, but is not limited to, at least one of data regarding drug prescriptions for the patient, data regarding fitness regime, or data regarding diet, and/or the like.

According to some embodiments, data segregation using a separate encryption key for each patient may be used over the first network transport link to ensure compliance with privacy and protection standards for medical or patient data. In some cases, sending the first patient data over the first network transport link to the at least one healthcare data system might comprise the first data collector publishing the first patient data via the computing system, while the at least one healthcare data system subscribes to the first patient data.

In some embodiments, the one or more patient devices might comprise at least one first patient device that is assigned to the first patient concurrent with the first data collector being assigned to the first patient, where the at least one first patient device might be pre-paired with the first data collector, enabling the at least one first patient device to automatically wirelessly communicate with the first data collector when both are activated at the first customer premises.

Alternatively, or additionally, the one or more patient devices might comprise at least one second patient device that is assigned to the first patient after the first data collector has been assigned to the first patient and has been collecting data from other patient devices among the one or more patient devices, where the at least one second patient device might each be added and registered as a new device that is associated with at least one of the first patient or the first data collector, enabling the at least one second patient device to automatically synchronize, and wirelessly communicate, with the first data collector when both are activated at the first customer premises.

Exemplary System and Hardware Implementation

Figure 5:
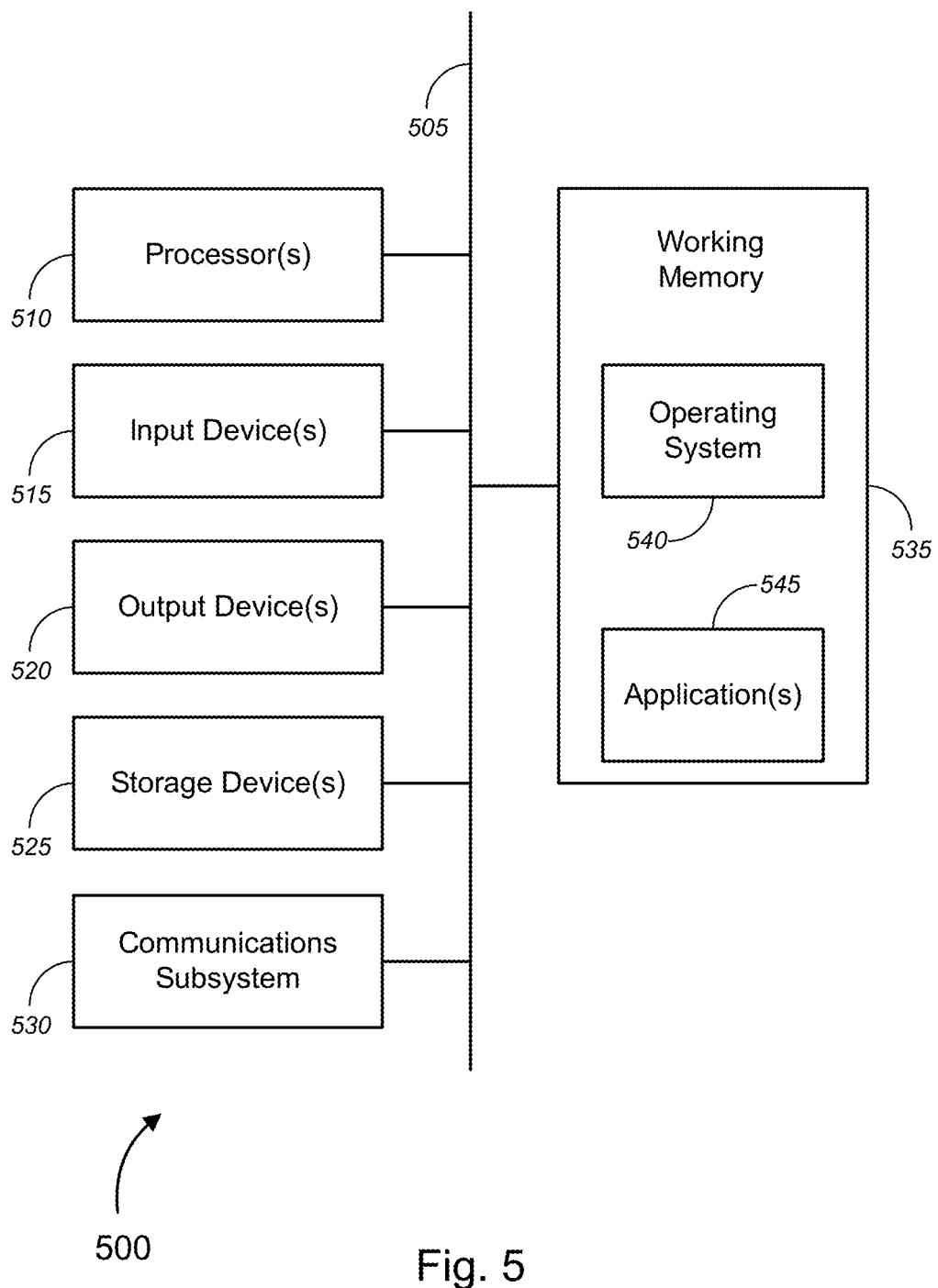
FIG. 5 is a block diagram illustrating an exemplary computer or system hardware architecture, in accordance with various embodiments.

FIG. 5 is a block diagram illustrating an exemplary computer or system hardware architecture, in accordance with various embodiments. FIG. 5 provides a schematic illustration of one embodiment of a computer system 500 of the service provider system hardware that can perform the methods provided by various other embodiments, as described herein, and/or can perform the functions of computer or hardware system (i.e., computing systems/customer premises equipment ("CPEs") 105, data collectors 115, patient devices 125, gateway devices 135, management consoles 150a, 150b, and 150, healthcare systems 160, and healthcare data systems 165 and 305, etc.), as described above. It should be noted that FIG. 5 is meant only to provide a generalized illustration of various components, of which one or more (or none) of each may be utilized as appropriate. FIG. 5, therefore, broadly illustrates how individual system elements may be implemented in a relatively separated or relatively more integrated manner.

The computer or hardware system 500—which might represent an embodiment of the computer or hardware system (i.e., computing systems/CPEs 105, data collectors 115, patient devices 125, gateway devices 135, management consoles 150a, 150b, and 150, healthcare systems 160, and healthcare data systems 165 and 305, etc.), described above with respect to FIGS. 1-4—is shown comprising hardware elements that can be electrically coupled via a bus 505 (or may otherwise be in communication, as appropriate). The hardware elements may include one or more processors 510, including, without limitation, one or more general-purpose processors and/or one or more special-purpose processors (such as microprocessors, digital signal processing chips, graphics acceleration processors, and/or the like); one or more input devices 515, which can include, without limitation, a mouse, a keyboard, and/or the like; and one or more output devices 520, which can include, without limitation, a display device, a printer, and/or the like.

The computer or hardware system 500 may further include (and/or be in communication with) one or more storage devices 525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 500 might also include a communications subsystem 530, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 530 may permit data to be exchanged with a network (such as the network described below, to name one example), with other computer or hardware systems, and/or with any other devices described herein. In many embodiments, the computer or hardware system 500 will further comprise a working memory 535, which can include a RAM or ROM device, as described above.

The computer or hardware system 500 also may comprise software elements, shown as being currently located within the working memory 535, including an operating system 540, device drivers, executable libraries, and/or other code, such as one or more application programs 545, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 525 described above. In some cases, the storage medium might be incorporated within a computer system, such as the system 500. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 500 and/or might take the form of source and/or installable code, which, upon compilation and/or installation on the computer or hardware system 500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 500) to perform methods in accordance with various embodiments of the invention. According to a set of embodiments, some or all of the procedures of such methods are performed by the computer or hardware system 500 in response to processor 510 executing one or more sequences of one or more instructions (which might be incorporated into the operating system 540 and/or other code, such as an application program 545) contained in the working memory 535. Such instructions may be read into the working memory 535 from another computer readable medium, such as one or more of the storage device(s) 525. Merely by way of example, execution of the sequences of instructions contained in the working memory 535 might cause the processor(s) 510 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 500, various computer readable media might be involved in providing instructions/code to processor(s) 510 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 525. Volatile media includes, without limitation, dynamic memory, such as the working memory 535. In some alternative embodiments, a computer readable medium may take the form of transmission media, which includes, without limitation, coaxial cables, copper wire, and fiber optics, including the wires that comprise the bus 505, as well as the various components of the communication subsystem 530 (and/or the media by which the communications subsystem 530 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 500. These signals, which might be in the form of electromagnetic signals, acoustic signals, optical signals, and/or the like, are all examples of carrier waves on which instructions can be encoded, in accordance with various embodiments of the invention.

The communications subsystem 530 (and/or components thereof) generally will receive the signals, and the bus 505 then might carry the signals (and/or the data, instructions, etc. carried by the signals) to the working memory 535, from which the processor(s) 505 retrieves and executes the instructions. The instructions received by the working memory 535 may optionally be stored on a storage device 525 either before or after execution by the processor(s) 510.

Figure 6:
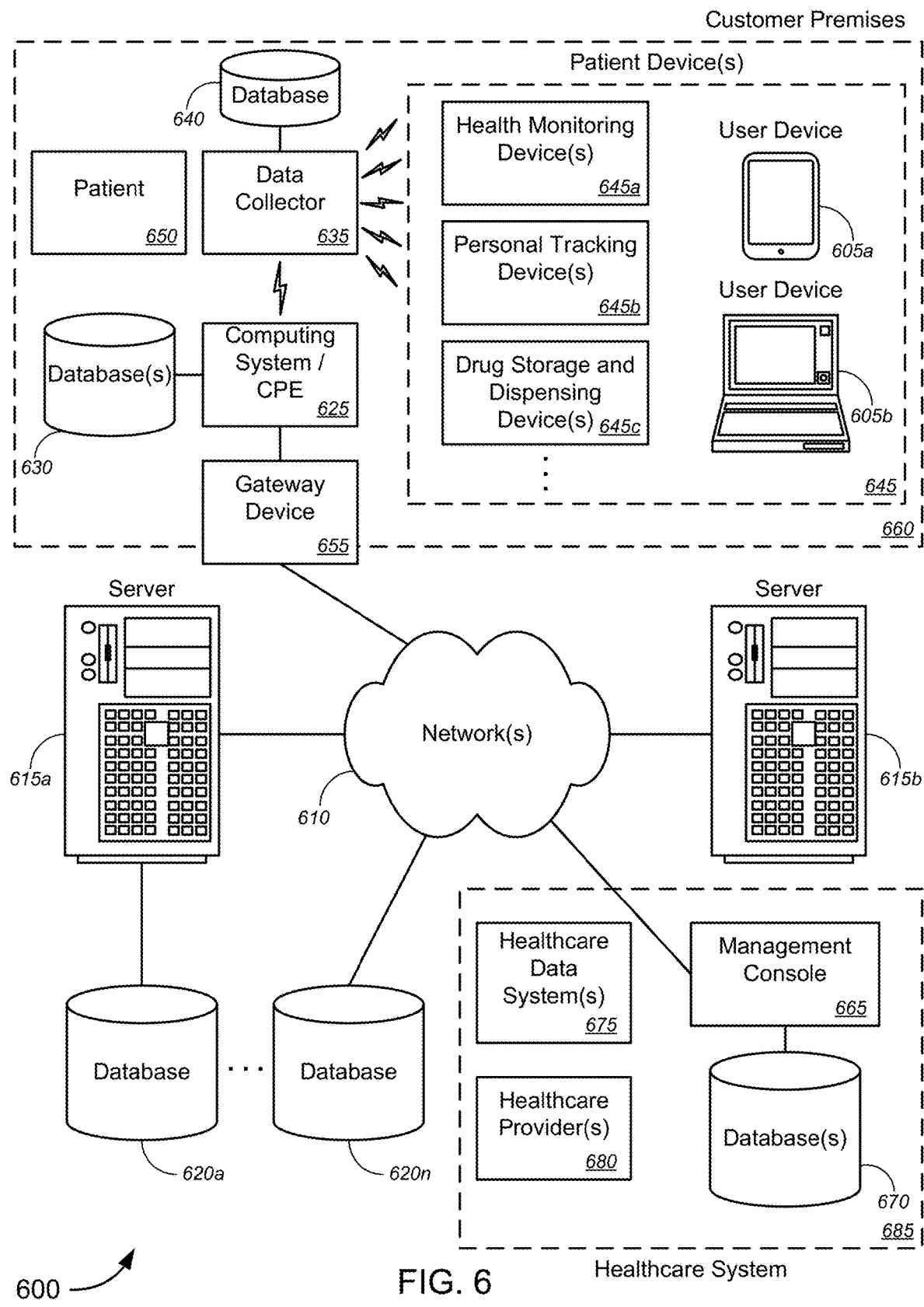
FIG. 6 is a block diagram illustrating a networked system of computers, computing systems, or system hardware architecture, which can be used in accordance with various embodiments.

As noted above, a set of embodiments comprises methods and systems for implementing health monitoring of patients, and, more particularly, to methods, systems, and apparatuses for implementing home health monitoring of patients via extension of healthcare system network into customer premises. FIG. 6 illustrates a schematic diagram of a system 600 that can be used in accordance with one set of embodiments. The system 600 can include one or more user computers, user devices, or customer devices 605. A user computer, user device, or customer device 605 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 605 can also have any of a variety of applications, including one or more applications configured to perform methods provided by various embodiments (as described above, for example), as well as one or more office applications, database client and/or server applications, and/or web browser applications. Alternatively, a user computer, user device, or customer device 605 can be any other electronic device, such as a thin-client computer, Internet-enabled mobile telephone, and/or personal digital assistant, capable of communicating via a network (e.g., the network(s) 610 described below) and/or of displaying and navigating web pages or other types of electronic documents. Although the exemplary system 600 is shown with two user computers, user devices, or customer devices 605, any number of user computers, user devices, or customer devices can be supported.

Certain embodiments operate in a networked environment, which can include a network(s) 610. The network(s) 610 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 610 (similar to network(s) 145 of FIG. 1, networks 205, 210, 215, and 235 of FIG. 2, network(s) 335 of FIG. 3, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 615. Each of the server computers 615 may be configured with an operating system, including, without limitation, any of those discussed above, as well as any commercially (or freely) available server operating systems. Each of the servers 615 may also be running one or more applications, which can be configured to provide services to one or more clients 605 and/or other servers 615.

Merely by way of example, one of the servers 615 might be a data server, a web server, a cloud computing device(s), or the like, as described above. The data server might include (or be in communication with) a web server, which can be used, merely by way of example, to process requests for web pages or other electronic documents from user computers 605. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 605 to perform methods of the invention.

The server computers 615, in some embodiments, might include one or more application servers, which can be configured with one or more applications accessible by a client running on one or more of the client computers 605 and/or other servers 615. Merely by way of example, the server(s) 615 can be one or more general purpose computers capable of executing programs or scripts in response to the user computers 605 and/or other servers 615, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 605 and/or another server 615. In some embodiments, an application server can perform one or more of the processes for implementing health monitoring of patients, and, more particularly, to methods, systems, and apparatuses for implementing home health monitoring of patients via extension of healthcare system network into customer premises, as described in detail above. Data provided by an application server may be formatted as one or more web pages (comprising HTML, JavaScript, etc., for example) and/or may be forwarded to a user computer 605 via a web server (as described above, for example). Similarly, a web server might receive web page requests and/or input data from a user computer 605 and/or forward the web page requests and/or input data to an application server. In some cases, a web server may be integrated with an application server.

In accordance with further embodiments, one or more servers 615 can function as a file server and/or can include one or more of the files (e.g., application code, data files, etc.) necessary to implement various disclosed methods, incorporated by an application running on a user computer 605 and/or another server 615. Alternatively, as those skilled in the art will appreciate, a file server can include all necessary files, allowing such an application to be invoked remotely by a user computer, user device, or customer device 605 and/or server 615.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 620a-620n (collectively, "databases 620"). The location of each of the databases 620 is discretionary: merely by way of example, a database 620a might reside on a storage medium local to (and/or resident in) a server 615a (and/or a user computer, user device, or customer device 605). Alternatively, a database 620n can be remote from any or all of the computers 605, 615, so long as it can be in communication (e.g., via the network 610) with one or more of these. In a particular set of embodiments, a database 620 can reside in a storage-area network ("SAN") familiar to those skilled in the art. (Likewise, any necessary files for performing the functions attributed to the computers 605, 615 can be stored locally on the respective computer and/or remotely, as appropriate.) In one set of embodiments, the database 620 can be a relational database, such as an Oracle database, that is adapted to store, update, and retrieve data in response to SQL-formatted commands. The database might be controlled and/or maintained by a database server, as described above, for example.

According to some embodiments, system 600 might further comprise a computing system or customer premises equipment ("CPE") 625 (similar to computing system 105 of FIG. 1, or the like) and corresponding database(s) 630 (similar to database(s) 110 of FIG. 1, or the like). System 600 might further comprise a data collector 635 (similar to data collector 115 of FIG. 1, or the like) and corresponding database 640 (similar to databases 120 and 320 of FIGS. 1 and 3, or the like). System 600 might further comprise one or more patient devices 645 that are associated with and assigned to a patient 650, each of the one or more patient devices 645 including, but not limited to, at least one of one or more health monitoring devices 645a, one or more personal tracking devices 645b, one or more drug storage and dispensing devices 645c, one or more patient user devices 605a and 605b, or one or more other patient devices (not shown), and/or the like (collectively, "patient devices 645" or "doctor-prescribed devices 645" or the like).

System 600 might further comprise a gateway device 655 (similar to gateway device 135 of FIG. 1, or the like), which might include, without limitation, at least one of a residential gateway ("RG") device, a business gateway ("BG") device, a virtual gateway ("VG") device, a network interface device, an optical network terminal, a home Internet router, an Internet modem, or other gateway device, and/or the like. In some instances, the computing system 625 and corresponding database(s) 630, the data collector 635 and corresponding database 640, and the gateway device 655 may be located or disposed within a customer premises 660 (similar to customer premises 140 of FIG. 1, or the like), which might include, but is not limited to, one of a single family house, a multi-dwelling unit ("MDU") within a multi-dwelling complex (including, but not limited to, an apartment building, an apartment complex, a condominium complex, a townhouse complex, a mixed-use building, etc.), a motel, an inn, a hotel, an office building or complex, a commercial building or complex, an industrial building or complex, and/or the like. The one or more patient devices 645 assigned to (and used to monitor) the patient 650 may be located or disposed at the customer premises 660, but may be designed or configured to be mobile, so as to monitor the patient 650 outside the customer premises 660. Although FIG. 6 depicts the computing system 625 and the gateway device 655 as distinct pieces of equipment, the various embodiments are not so limited, and the computing system 625 and the gateway device 655 either may be separate and interconnected devices within the customer premises 660 or may be integrated within a single device (not shown) within the customer premises 660.

In some embodiments, each of at least one first patient device 645 among the one or more patient devices 645 might be wirelessly paired, synced, or synchronized with the data collector 635. In some cases, where the at least one first patient device 645 is assigned to the patient 650 concurrent with the data collector 635 being assigned to the patient 650, the at least one first patient device 645 may be pre-paired with the data collector 635, enabling the at least one first patient device 645 to automatically wirelessly communicate with the data collector 635 when both are (simultaneously or concurrently) activated at the customer premises 660. Alternatively, where the at least one first patient device 645 is assigned to the patient 650 after the data collector 635 has been assigned to the patient 635 and has been collecting data from other patient devices 645 among the one or more patient devices 645, the at least one first patient device 645 may each be added and registered as a new device that is associated with at least one of the patient 650 or the data collector 635, enabling the at least one first patient device 645 to automatically synchronize, and wirelessly communicate, with the data collector 635 when both are (simultaneously or concurrently) activated at the customer premises 660.

System 600 might further comprise a management console 665 (similar to management console 150a or 150b of FIG. 1 or management console 150 of FIG. 2, or the like) and corresponding database(s) 670 (similar to database(s) 155a or 155b of FIG. 1, or the like). According to some embodiments, the management console 665 might include, but is not limited to, at least one of a controller of a healthcare data management system, a secure server computer, a distributed computing system, or a cloud computing system, and/or the like. In some instances, the management console 665 and corresponding database(s) 670 might be part of or disposed within a healthcare system 685 (similar to healthcare system 160 of FIG. 1, or the like) (such as shown in FIG. 6, or the like). Alternatively, or additionally, the management console 665 and corresponding database(s) 670 might be disposed external to the healthcare system 685 (not shown in FIG. 6), in some cases, as part of at least one network 610 among the one or more networks 610 that is operated by a network, computing, and/or cloud service provider(s). According to some embodiments, the healthcare system 685 might refer to at least one of a single healthcare facility, a collection of interconnected healthcare facilities (whether physically interconnected, connected via computing systems and wide area networks ("WAN"), and/or configured to securely communicate sensitive data with each other, or the like), a healthcare computing system, or a healthcare data network system, and/or the like. Healthcare system 685 might include, without limitation, one or more healthcare data systems 675 (similar to healthcare data systems 165 and 165a-165d of FIG. 1, or the like) that may be accessible by or associated with one or more healthcare providers 680 (similar to healthcare providers 170a-170n of FIG. 1, or the like). In some embodiments, the one or more healthcare data systems 675 might include, without limitation, at least one of an electronic medical record ("EMR") system, an electronic health record ("EHR") system, one or more healthcare servers, or one or more healthcare provider user devices, and/or the like. In some instances, the one or more healthcare providers 680 might include, but are not limited to, at least one of a physician, a doctor, a surgeon, a nurse practitioner, a nurse, a medical assistant, a clinical receptionist, a pharmacist, a medical laboratory technician, a healthcare scheduler, or a health insurance agent, and/or the like.

Herein, "EMR" might refer to a digital version of a patient's chart, might contain the patient's medical and treatment history with a single healthcare provider, a single group of healthcare providers, or a single healthcare facility, and typically might not be shared with external healthcare providers or facilities. By contrast, "EHR" might refer to the patient's records from multiple healthcare providers, multiple groups of healthcare providers, or multiple healthcare facilities, might include the patient's personal information, the patient's demographics, test results, medical history, history of present illness, medications, allergies, immunization status, laboratory test results, radiology images, vital signs, billing information, and/or the like, and might follow the patient from healthcare provider/facility to healthcare provider/facility. Although FIG. 6 depicts a single patient's data collector 635 and patient device(s) 645 being communicatively coupled via computing system 625, gateway device 655, and network(s) 610 to management console 665 and to healthcare data system(s) 675, this is merely to simplify illustration, and the various embodiments are not so limited. Rather, management console 665 and healthcare data system(s) 675 are configured, and designed, to communicatively couple with one or more patient devices 645 assigned to each of a plurality of patients 650 who are located, or who reside, at geographically separate customer premises 660 (not limited to the same city, state/province, country, or region as the healthcare data system(s) 675).

In a non-limiting example, to properly assess the health of a patient 650, a healthcare provider 680 (e.g., a doctor, or the like) might hand out, assign, or prescribe one or more first patient devices 645 (and perhaps a data collector 635 as well) to the patient 650. The patient 650 would be asked to wear or attach the one or more first patient devices 645 on the patient's body or clothing (or to implant the one or more first patient devices 645 in the patient's body), the one or more first patient devices 645 being registered on a healthcare data system(s) 675 and/or the management console 665 as being associated with the patient 650. The management console 665 or the system might then extend the healthcare system network to each customer local area network in a customer premises 660 of the patient 650 among a plurality of customer local area networks in corresponding customer premises 660 associated with a corresponding plurality of patients 650, in the manner described below. In this way, patient privacy and security, as well as compliance with standards such as the standards set out in the health insurance portability and accountability act ("HIPAA") may be achieved.

That is, in operation, when the patient 650 returns to the patient's customer premises 660 with the assigned one or more first patient devices 645 (and, in some cases, the assigned data collector 635 as well), where the one or more first patient devices 645 are assigned to the patient 650 concurrent with the data collector 635 being assigned to the patient 650, the one or more first patient devices 645 may be pre-paired with the data collector 635, enabling the one or more first patient devices 645 to automatically wirelessly communicate with the data collector 635 when both are (simultaneously or concurrently) activated at the customer premises 660. Alternatively, where the one or more first patient devices 645 are assigned to the patient 650 after the data collector 635 has been assigned to the patient 635 and has been collecting data from other patient devices 645 among the one or more patient devices 645, the one or more first patient devices 645 may each be added and registered as a new device that is associated with at least one of the patient 650 or the data collector 635, enabling the one or more first patient devices 645 to automatically synchronize, and wirelessly communicate, with the data collector 635 when both are (simultaneously or concurrently) activated at the customer premises 660.

Once paired, the data collector 635 might establish a paired wireless link (depicted in FIG. 6 by lightning bolt symbols) between the data collector 635 and each of at least one patient device 645 among one or more patient devices 645 assigned to the patient 650. In some instances, the at least one data collector 635 might include, but is not limited to, a unique authentication token that is hard-coded in the at least one data collector 635. The data collector 635 might receive and collect first patient data from each of at least one patient device 645 among the one or more patient devices 645 over the corresponding paired wireless link. In some instances, the first patient data might include, but is not limited to, at least one of data regarding physiology of the patient, health tracking data of the patient, or data regarding a health alert associated with the patient, and/or the like. In some cases, the first patient data might be encrypted at each of the at least one patient device 645 prior to sending to the data collector 635. Computing system 625 might establish a wireless link (depicted in FIG. 6 by the lightning bolt symbol) between the computing system 625 and the data collector 635, which might relay the collected first patient data to the computing system 625 via the established wireless link. In some embodiments, the paired wireless link (between the data collector 635 and each of at least one patient device 645) and/or the wireless link (between the computing system 625 and the data collector 635) might each include, without limitation, at least one of a Bluetooth wireless link, a WiFi wireless link, a ZigBee wireless link, or Z-wave wireless link, and/or the like. The computing system 625 might receive, from the data collector 635, the first patient data obtained by at least one patient device 645 that is associated with and assigned to the patient 650.

At least one of the computing system 625 or the management console 665 might establish a first network transport link between the computing system 625 and at least one healthcare data system 675 (e.g., via the gateway device 655, network(s) 610, and the healthcare system 685, or the like) that is accessible by or associated with one or more healthcare providers 680. According to some embodiments, the first network transport link might include, without limitation, at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system 675 is disposed, and/or the like. At least one of the computing system 625 or the management console 665 might send the first patient data over the first network transport link to the at least one healthcare data system 675. The management console 665 might store the first patient data in the at least one healthcare data system 675, the first patient data being secured within a portion of the at least one healthcare data system 675 that is allocated to information regarding the patient 650 (such as shown and described in detail with respect to FIG. 3, or the like). In some embodiments, the first network transport link might be configured as a one-way network transport link that enables storage of the first patient data from the data collector 635 to the at least one healthcare data system 675 while preventing access to any data stored in the at least one healthcare data system 675 via the first network transport link.

In some embodiments, the management console 665 might establish a second network transport link between the management console 665 and at least one of the computing system 625 or the first data collector 635. In some cases, the second network transport link, like the first network transport link, might include, without limitation, at least one of a VPN, a SD-LAN, a SD-WAN, or a virtual extension of the healthcare provider network in which the at least one healthcare data system is disposed, and/or the like. In some instances, the management console 665 might provide patient device data to the at least one of the computing system 625 or the data collector 635 over the second network transport link, the patient device data comprising a list of authorized patient devices among the one or more patient devices 645 that are associated with and assigned to the patient 650. In some cases, providing the patient device data might comprise at least one of sending the patient device data to the computing system 625 or providing the computing system 625 with access over the second network transport link to a database (e.g., database(s) 670a or 670b, or the like) containing the list of authorized patient devices associated with and assigned to the patient. In some instances, the at least one of the computing system 625 or the data collector 635 might prevent collection of data, or prevent communication of data (to the computing system 625 and/or to the data collector 635), from devices that are not listed in the patient device data as being authorized. In some embodiments, the second network transport link and the first network transport link might be the same network transport link (e.g., as shown and described with respect to FIG. 2, or the like), while, in alternative embodiments, the second network transport link might be different or separate from the first network transport link (e.g., as shown and described with respect to FIG. 3, or the like). According to some embodiments, the management console 665 might send communications data to at least one patient device 645 among the one or more patient devices 645 via the computing system 625 over the second network transport link. In some instances, the communications data might include, without limitation, at least one of data regarding drug prescriptions for the patient, data regarding fitness regime, or data regarding diet, and/or the like.

These and other functions of the system 600 (and its components) are described in greater detail above with respect to FIGS. 1-4.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
receiving, with a computing system and from a first data collector, first patient data obtained by one or more patient devices that are associated with and assigned to a first patient, the first patient data being wirelessly collected from the one or more patient devices by the first data collector, the first data collector being assigned to the first patient, wherein the computing system and the first data collector are both located at a first customer premises associated with the first patient;
establishing, with at least one of the computing system or a management console, a first network transport link between the computing system and at least one healthcare data system that is accessible by or associated with one or more healthcare providers, wherein the first network transport link is configured as a one-way network transport link that allows communication from the computing system to and from the at least one healthcare data system and prevents access to any data stored in the at least one healthcare data system via the first network transport link;
sending, with at least one of the computing system or the management console, the first patient data over the first network transport link to the at least one healthcare data system; and
storing, with the management console, the first patient data in the at least one healthcare data system, the first patient data being secured within a portion of the at least one healthcare data system that is allocated to information regarding the first patient.

2. The method of claim 1, wherein the computing system comprises at least one of customer premises equipment ("CPE"), universal CPE ("uCPE"), a software-defined wide area network ("SD-WAN") uCPE, a customer premises-based computing system, network interface device, or an optical network terminal.

3. The method of claim 1, wherein the management console comprises at least one of a controller of a healthcare data management system, a secure server computer, a distributed computing system, or a cloud computing system.

4. The method of claim 1, wherein the one or more patient devices each comprises at least one of one or more health monitoring devices, one or more thermometers, one or more drug delivery devices, one or more personal tracking devices, an insulin pump, a pace maker, one or more drug storage and dispensing devices, or one or more patient user devices.

5. The method of claim 1, wherein the first patient data comprises at least one of data regarding physiology of the patient, health tracking data of the patient, or data regarding a health alert associated with the patient.

6. The method of claim 1, wherein the at least one healthcare data system comprises at least one of an electronic medical record ("EMR") system, an electronic health record ("EHR") system, one or more healthcare servers, or one or more healthcare provider user devices, wherein the one or more healthcare providers comprise at least one of a physician, a doctor, a surgeon, a nurse practitioner, a nurse, a medical assistant, a clinical receptionist, a pharmacist, a medical laboratory technician, a healthcare scheduler, or a health insurance agent.

7. The method of claim 1, wherein the first network transport link further comprises at least one of a virtual private network ("VPN"), a software-defined local area network ("SD-LAN"), a software-defined wide area network ("SD-WAN"), an Internet Protocol security ("IPsec") tunnel in the SD-LAN, an IPsec tunnel in the SD-WAN, or a virtual extension of a healthcare provider network in which the at least one healthcare data system is disposed.

8. The method of claim 1, wherein data segregation using a separate encryption key for each patient is used over the first network transport link to ensure compliance with privacy and protection standards for medical or patient data.

9. The method of claim 1, wherein sending the first patient data over the first network transport link to the at least one healthcare data system comprises the first data collector publishing the first patient data via the computing system, and wherein the at least one healthcare data system subscribes to the first patient data.

10. The method of claim 1, wherein the one or more patient devices comprise at least one first patient device that is assigned to the first patient concurrent with the first data collector being assigned to the first patient, wherein the at least one first patient device is pre-paired with the first data collector, enabling the at least one first patient device to automatically wirelessly communicate with the first data collector when both are activated at the first customer premises.

11. The method of claim 1, wherein the one or more patient devices comprise at least one second patient device that is assigned to the first patient after the first data collector has been assigned to the first patient and has been collecting data from other patient devices among the one or more patient devices, wherein the at least one second patient device is each added and registered as a new device that is associated with at least one of the first patient or the first data collector, enabling the at least one second patient device to automatically synchronize, and wirelessly communicate, with the first data collector when both are activated at the first customer premises.

12. The method of claim 1, further comprising:
establishing, with the computing system, a wireless link between the computing system and the first data collector, wherein the first patient data is encrypted at each of the one or more patient devices, and wherein the first data collector receives the first patient data that has been encrypted over a paired wireless link between the first data collector and each corresponding patient device among the one or more patient devices, wherein the first data collector relays the collected first patient data to the computing system via the established wireless link.

13. The method of claim 12, wherein the wireless link comprises at least one of a Bluetooth wireless link, a WiFi wireless link, a ZigBee wireless link, or Z-wave wireless link.

14. The method of claim 1, wherein the at least one first data collector comprises a unique authentication token that is hard-coded.

15. The method of claim 1, further comprising:
establishing, with the management console, a second network transport link between the management console and at least one of the computing system or the first data collector; and
providing, with the management console, patient device data to the at least one of the computing system or the first data collector over the second network transport link, the patient device data comprising a list of authorized patient devices among the one or more patient devices that are associated with and assigned to the first patient, wherein providing the patient device data comprises at least one of sending the patient device data to the computing system or providing the computing system with access over the second network transport link to a database containing the list of authorized patient devices associated with and assigned to the first patient, wherein the at least one of the computing system or the first data collector prevents collection of data, or prevents communication of data, from devices that are not listed in the patient device data.

16. The method of claim 15, further comprising:
sending, with the management console, communications data to at least one patient device among the one or more patient devices via the computing system, wherein the communications data comprises at least one of data regarding drug prescriptions for the patient, data regarding fitness regime, or data regarding diet.

17. A system, comprising:
a computing system, comprising:
at least one first processor; and
a first non-transitory computer readable medium communicatively coupled to the at least one first processor, the first non-transitory computer readable medium having stored thereon computer software comprising a first set of instructions that, when executed by the at least one first processor, causes the computing system to:
receive, from a first data collector, first patient data obtained by one or more patient devices that are associated with and assigned to a first patient, the first patient data being wirelessly collected from the one or more patient devices by the first data collector, the first data collector being assigned to the first patient, wherein the computing system and the first data collector are both located at a first customer premises associated with the first patient;
a management console, comprising:
at least one second processor; and
a second non-transitory computer readable medium communicatively coupled to the at least one second processor, the second non-transitory computer readable medium having stored thereon computer software comprising a second set of instructions that, when executed by the at least one second processor, causes the management console to:
establish a first network transport link between the computing system and at least one healthcare data system that is accessible by or associated with one or more healthcare providers, wherein the first network transport link is configured as a one-way network transport link that allows communication from the computing system to and from the at least one healthcare data system and prevents access to any data stored in the at least one healthcare data system via the first network transport link;
send the first patient data over the first network transport link to the at least one healthcare data system; and
store the first patient data in the at least one healthcare data system, the first patient data being secured within a portion of the at least one healthcare data system that is allocated to information regarding the first patient.

18. The system of claim 17, wherein the computing system comprises at least one of customer premises equipment ("CPE"), universal CPE ("uCPE"), a software-defined wide area network ("SD-WAN") uCPE, a customer premises-based computing system, network interface device, or an optical network terminal, wherein the management console comprises at least one of a controller of a healthcare data management system, a secure server computer, a distributed computing system, or a cloud computing system.

19. The system of claim 17, wherein the one or more patient devices each comprises at least one of one or more health monitoring devices, one or more thermometers, one or more drug delivery devices, one or more personal tracking devices, an insulin pump, a pace maker, one or more drug storage and dispensing devices, or one or more patient user devices, wherein the at least one healthcare data system comprises at least one of an electronic medical record ("EMR") system, an electronic health record ("EHR") system, one or more healthcare servers, or one or more healthcare provider user devices, wherein the one or more healthcare providers comprise at least one of a physician, a doctor, a surgeon, a nurse practitioner, a nurse, a medical assistant, a clinical receptionist, a pharmacist, a medical laboratory technician, a healthcare scheduler, or a health insurance agent.

* * * * *